(12) United States Patent
Sahara et al.

(10) Patent No.: US 7,371,847 B2
(45) Date of Patent: May 13, 2008

(54) YEAST-ORIGIN PROMOTER AND VECTOR AND EXPRESSION SYSTEM USING THE SAME

(75) Inventors: Takehiko Sahara, Hokkaido (JP); Satoru Ohgiya, Hokkaido (JP); Takako Goda, Hokkaido (JP); Kosei Kawasaki, Hokkaido (JP)

(73) Assignee: National Institute of Advanced Industrial Science and Technology, Chiyoda-ku (JP)

( * ) Notice: Subject to any disclaimer, the term of this patent is extended or adjusted under 35 U.S.C. 154(b) by 176 days.

(21) Appl. No.: 10/519,545

(22) PCT Filed: May 13, 2003

(86) PCT No.: PCT/JP03/05956

§ 371 (c)(1),
(2), (4) Date: Dec. 28, 2004

(87) PCT Pub. No.: WO2004/003197

PCT Pub. Date: Jan. 8, 2004

(65) Prior Publication Data

US 2005/0260590 A1    Nov. 24, 2005

(30) Foreign Application Priority Data

Jun. 28, 2002    (JP)    ............... 2002-191383

(51) Int. Cl.
| | |
|---|---|
| *C07H 21/04* | (2006.01) |
| *C12Q 1/68* | (2006.01) |
| *C12N 1/15* | (2006.01) |
| *C12N 15/63* | (2006.01) |
| *C12N 1/00* | (2006.01) |

(52) U.S. Cl. .................. 536/24.1; 435/6; 435/254.11; 435/320.1

(58) Field of Classification Search ...................... None
See application file for complete search history.

(56) References Cited

OTHER PUBLICATIONS

Nakagawa et al. Mga2p is a Putative Sensor for Low Temperature and Oxygen to Induce OLE1 Transcription in *Saccharomyces cerevisiae*. Biochem. and Biophys. Res. Comm. 291: 707-713. 2002.*

Goldenberg et al. Role of *Escherichia coli* cspA promoter sequences and adaptation of translational apparatus in the cold shock response. Mol. Gen. Genet. 256: 282-290. 1997.*
Lim et al. Low Temperature Reulated DEAD-box RNA Helicase from the Antartic Archaeon, *Methanococcoides burtonii*. J. Mol. Biol. 297: 553-567. 2000.*
Database WPI Derwent Publications Ltd., London, GB; AN 1996-110275; XP002337559 "Novel yeast promoter active at low temperatures—comprises the Lg-CSP1 promoter region from *S cerevisiae*", & JP 08 009977 A (Kirin Brewery) Jan. 16, 1996 *Abstract*.
Qoronfleh M Walid et al., "Identification and characterization of novel low-temperature-inducible promoters of *Escherichia coli*", Journal of Bacteriology, vol. 174, No. 24, 1992, pp. 7902-7909.
Muiacic M et al., "Cold-inducible cloning vectors for low-temperature protein expression in *Escherichia coli*: application to the production of a toxic and proteolytically sensitive fusion protein", GENE, vol. 238, No. 2, 1999, pp. 325-332.
International Search Report of PCT/JP03/05956.
J.C. Varela et al., "The *Saccaromyces cerevisiae* HSP12 gene is activated by the high-osmolarity glycerol pathway and negatively regulated by protein kinase A", Mol. Cell. Biol., 1995, vol. 15, No. 11, pp. 6232-6245.
E. De Groot et al., "Very low amounts of glucose cause repression of the stress-responsive gene HSP12 in *Saccharomyces cervisiae*", Microbiology, 2000, vol. 146, No. 2, pp. 367-375.
T. Sahara et al., "Comprehensive expression analysis of time-dependent genetic responses in yeast cells to low temperature", J. Biol. Chem., Dec. 2002, vol. 277, No. 51, pp. 50015-50021.
L. Zhang et al., "Multiple mechanisms regulate expression of low temperature responsive (LOT) genes in *Saccharomyces cerevisiae*", Biochem Biophys Res Commun, 2001, vol. 283, No. 2, pp. 531-535.
Agustin Aranda et al., "Correlation between acetaldehyde and ethanol resistance and expression of HSP genes in yeast strains isolated during the biological aging of sherry wines", Arch Microbiol (2002) 177: 304-312.
Sonia Rodriguez-Vargas et al., "Gene Expression Analysis of Cold and Freeze Stress in Baker's Yeast", Applied and Environmental Microbiology, vol. 68, No. 6, Jun. 2002, p. 3024-3030.

* cited by examiner

*Primary Examiner*—David Guzo
*Assistant Examiner*—Michele K. Joike
(74) *Attorney, Agent, or Firm*—Foley & Lardner LLP

(57) ABSTRACT

The present invention provides a DNA fragment having a cold-inducible promoter function of yeast, which has high activity in a low temperature range, by identifying a DNA fragment, which exists in a non-translation region located upstream of the 5'-terminal side of a gene selected from the group consisting of cold-inducible genes of *Saccharomyces cerevisiae*, and has a cold-inducible promoter function.

46 Claims, 26 Drawing Sheets
(1 of 26 Drawing Sheet(s) Filed in Color)

Probe: NSR1

Probe: ACT1

RPC19-DBP2 IGR Forward
Probe: GFPuv

RPC19-DBP2 IGR Reverse
Probe: GFPuv

PDX3-HMT1 IGR Forward
Probe: GFPuv

PDX3-HMT1 IGR Reverse
Probe: GFPuv

-610 HSP12 IGR Forward
Probe: GFPuv

-610 HSP12 IGR Reverse
Probe: GFPuv

Total RNA: 10 μg

Total Protein: 10 μg

Total Protein: 2 μg

Total Protein: 2 μg

Total Protein: 10 μ g

ECFP     DsRed

SEQUENCE LISTING

```
<160> NUMBER OF SEQ ID NOS: 34

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence:primer

<400> SEQUENCE: 1
atgtctgacg caggtagaaa ag                                              22

<210> SEQ ID NO 2
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 2
ttacttcttg gttgggtctt cttc                                            24

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 3
ggatgactta cggtggtaga gatc                                            24

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence:primer

<400> SEQUENCE: 4
aagatacctc tggcggccac                                                 20

<210> SEQ ID NO 5
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 5
```

-continued

```
ggtaacaaga aggaagttaa ggcttc                                           26

<210> SEQ ID NO 6
<211> LENGTH: 23
<212> TYPE: DNA
<213> ORGANISM: Artificial Sequence
<220> FEATURE:
<223> OTHER INFORMATION: Description of Artificial Sequence:primer

<400> SEQUENCE: 6
tgttttcttt gaaccagcga aag                                              23

<210> SEQ ID NO 7
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 7
ggtttctgtg gagtttttac aggag                                            25

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence:primer

<400> SEQUENCE: 8
gcgaatattt agtgactact tcgtcc                                           26

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 9
tggacgatac aataatttcg tacca                                            25

<210> SEQ ID NO 10
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 10
caacctggtt cctataaaaa atgtctt                                          27

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 11
ggaagcttat gccaacttct ggaactacta tt                                    32

<210> SEQ ID NO 12
<211> LENGTH: 33
<212> TYPE: DNA
```

```
<213> ORGANISM: Artificial Sequence
<220> FEATURE:
<223> OTHER INFORMATION: Description of Artificial Sequence:primer

<400> SEQUENCE: 12
ggaagctttt aaaagaactt accagtttcg tag                                    33

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 13
tcaaaaagac tcctacgttg gtgatgaagc                                        30

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 14
catacgcgca caaaagcaga gattagaaac                                        30

<210> SEQ ID NO 15
<211> LENGTH: 24
<212> TYPE: DNA
<213> ORGANISM: Artificial Sequence
<220> FEATURE:
<223> OTHER INFORMATION: Description of Artificial Sequence:primer

<400> SEQUENCE: 15
atgttacgga tcgactcaaa gacc                                              24

<210> SEQ ID NO 16
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 16
atttgctcta aatttgcctt aatagtgc                                          28

<210> SEQ ID NO 17
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 17
gggactgtta atgaaaaatt caatg                                             25

<210> SEQ ID NO 18
<211> LENGTH: 25
<212> TYPE: DNA
<213> ORGANISM: Artificial Sequence
<220> FEATURE:
<223> OTHER INFORMATION: Description of Artificial Sequence:primer

<400> SEQUENCE: 18
tattttcttt ggatgaattt gtcgg                                             25
```

```
<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 19
gatcccacta acggcccag                                                   19

<210> SEQ ID NO 20
<211> LENGTH: 28
<212> TYPE: DNA
<213> ORGANISM: Artificial Sequence
<220> FEATURE:
<223> OTHER INFORMATION: Description of Artificial Sequence:primer

<400> SEQUENCE: 20
tgttgtattt agtttttttt gttttgag                                         28

<210> SEQ ID NO 21
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 21
cagaaaattt ttccttcagt ttatttg                                          27

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 22
atcggcgtaa aaaaaaaaaa aaaaaaaaaa                                       30

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:primer

<400> SEQUENCE: 23
aacaactatt tttataacat ataatttccc                                       30

<210> SEQ ID NO 24
<211> LENGTH: 19
<212> TYPE: DNA
<213> ORGANISM: Artificial Sequence
<220> FEATURE:
<223> OTHER INFORMATION: Description of Artificial Sequence:primer

<400> SEQUENCE: 24
ctgcctactg ctcaccttg                                                   19

<210> SEQ ID NO 25
<211> LENGTH: 29
<212> TYPE: DNA
<213> ORGANISM: Artificial Sequence
<220> FEATURE:
```

<223> OTHER INFORMATION: Description of Artificial Sequence:primer

<400> SEQUENCE: 25
atgtctaaag gtgaagaatt attcactgg                          29

<210> SEQ ID NO 26
<211> LENGTH: 29
<212> TYPE: DNA
<213> ORGANISM: Artificial Sequence
<220> FEATURE:
<223> OTHER INFORMATION: Description of Artificial Sequence:primer

<400> SEQUENCE: 26
ttatttgtac aattcatcca taccatggg                          29

<210> SEQ ID NO 27
<211> LENGTH: 36
<212> TYPE: DNA
<213> ORGANISM: Artificial Sequence
<220> FEATURE:
<223> OTHER INFORMATION: Description of Artificial Sequence:linker

<400> SEQUENCE: 27
ccgctcgagc ggccgcgagc tcgtcgacat cgatgg                  36

<210> SEQ ID NO 28
<211> LENGTH: 36
<212> TYPE: DNA
<213> ORGANISM: Artificial Sequence
<220> FEATURE:
<223> OTHER INFORMATION: Description of Artificial Sequence:linker

<400> SEQUENCE: 28
ccatcgatgt cgacgagctc gcggccgctc gagcgg                  36

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence:primer

<400> SEQUENCE: 29
ggactagtga tcccactaac ggcccag                            27

<210> SEQ ID NO 30
<211> LENGTH: 36
<212> TYPE: DNA
<213> ORGANISM: Artificial Sequence
<220> FEATURE:
<223> OTHER INFORMATION: Description of Artificial Sequence:primer

<400> SEQUENCE: 30
cgggatcctg ttgtatttag ttttttttgt tttgag                  36

<210> SEQ ID NO 31
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 31
aaaaggatcc aaaaaaatgg tgagcaaggg cgaggag                 37

```
<210> SEQ ID NO 32
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 32
ttttaagctt ttacttgtac agctcgtcca t                              31

<210> SEQ ID NO 33
<211> LENGTH: 37
<212> TYPE: DNA
<213> ORGANISM: Artificial Sequence
<220> FEATURE:
<223> OTHER INFORMATION: Description of Artificial Sequence:primer

<400> SEQUENCE: 33
aaaaggatcc aaaaaaatgg cctcctccga ggacgtc                        37

<210> SEQ ID NO 34
<211> LENGTH: 31
<212> TYPE: DNA
<213> ORGANISM: Artificial Sequence
<220> FEATURE:
<223> OTHER INFORMATION: Description of Artificial Sequence:primer

<400> SEQUENCE: 34
aaaaaagctt ctacaggaac aggtggtggc g                              31
```

YEAST-ORIGIN PROMOTER AND VECTOR AND EXPRESSION SYSTEM USING THE SAME

The application contains at least one drawing executed in color. Copies of this patent or patent application publication with color drawing(s) will be provided by the Office upon request and payment of the necessary fee.

TECHNICAL FIELD

The present invention relates to a DNA fragment having a cold-inducible promoter function of yeast.

BACKGROUND ART

Yeast has widely been used for production of foods by fermentation, such as alcoholic beverages including beer or Japanese sake, or breads, for production of metabolites such as amino acids, and also as a host used for production of proteins of homogeneous or heterogeneous organisms using the recombinant DNA technique. The characteristics of yeast used in production of proteins by such recombinant DNA technology include: the safety of yeast as an organism, which is assumed from the past record in that yeast has previously been used in the food industry; a relatively high probability of success in the expression of proteins of animals such as a human because yeast is not a prokaryote such as *Escherichia coli*, but a eukaryote; and sufficiently developed gene recombination technology regarding yeast.

In general, it has been already known regarding production of beer or brewage that fermentation at a low temperature such as 10° C. or lower brings on exquisite flavor and taste, and that the quality as food can be improved. Since the existence of a chemical substance for improving flavor or taste is assumed from such improvement of flavor and taste, it is considered that the functions of a gene of an enzyme synthesizing such a chemical substance are appropriately regulated by decreasing the temperature. However, there is only a limited amount of information regarding genes of yeast functioning at a low temperature. Thus, the type of a gene that is important for improvement of the flavor or taste of foods is still unknown.

In gene recombination technology using yeast or *Escherichia coli* as a host, promoters functioning at an ordinary culture temperature (30° C. in the case of yeast and 37° C. in the case of *Escherichia coli*) have conventionally been used to produce proteins. In general, strong promoters producing a more large amount of mRNA have been used. It is considered that culture at a low temperature is disadvantageous in the production of proteins by genetic recombination. As a matter of fact, however, there are some cases where a low temperature is intentionally used to produce proteins. For example, when a protein produced at an ordinary temperature does not have a correct three-dimensional structure, a protein having a correct three-dimensional structure may be then produced at a low temperature. Thus, in order that a protein has a correct three-dimensional structure, there are some cases where production of a protein may be carried out at a culture temperature that is 10° C. lower than the ordinary temperature (Prot. Exp. Purif. 2, 432-441 (1991)). In addition, it is also expected that application of such a low temperature prevent the produced protein from being decomposed with protease of a host. Thus, it is considered that production of proteins at a low temperature has advantages. On the other hand, it is also considered that in the case of the currently used promoter functioning at an ordinary temperature, the promoter activity decreases together with a decrease in the temperature. Accordingly, it is appropriate to use a promoter exhibiting high activity in a low temperature range to establish an efficient protein production system at a low temperature.

To date, there has been a report that the mRNA of each of YBR067C (TIP1), YER011W (TIR1), YGR159C(NSR1), YGL055W (OLE1), YOR010C (TIR2), YKL060C (FBA1), YIL018W (RPL2B), YDL014W (NOP1), YKL183W, YKL011W, and YDR299W (BFR2), is increased by treating the yeast at a low temperature. However, the degree of cold inducibility of each of the promoters of the above genes has not yet been examined.

DISCLOSURE OF THE INVENTION

It is an object of the present invention to provide, for example, a DNA fragment having a cold-inducible promoter function of yeast, which has high activity in a low temperature range (e.g. 10° C. or lower), by identifying and analyzing a large number of cold-inducible genes of yeast.

As a result of intensive studies directed towards achieving the aforementioned object, the present inventors have identified genes of *Saccharomyces cerevisiae* exhibiting cold inducibility using a DNA microarray, and have found a DNA fragment having a cold-inducible promoter function in the non-translation region located upstream of the 5'-terminal side of each gene, thereby completing the present invention.

That is to say, the present invention relates to a DNA fragment, which exists in the non-translation region located upstream of the 5'-terminal side of a gene selected from the group consisting of genes of *Saccharomyces cerevisiae* described in Table 1 indicated below, and has a cold-inducible promoter function.

TABLE 1

| No. | Systematic gene name |
|---|---|
| 1 | YAL014C |
| 2 | YAL015C |
| 3 | YAL025C |
| 4 | YAL034C |
| 5 | YBL048W |
| 6 | YBL049W |
| 7 | YBL054W |
| 8 | YBL056W |
| 9 | YBL065W |
| 10 | YBL078C |
| 11 | YBR016W |
| 12 | YBR018C |
| 13 | YBR024W |
| 14 | YBR034C |
| 15 | YBR045C |
| 16 | YBR047W |
| 17 | YBR050C |
| 18 | YBR072W |
| 19 | YBR116C |
| 20 | YBR117C |
| 21 | YBR126C |
| 22 | YBR148W |
| 23 | YBR199W |
| 24 | YBR223C |
| 25 | YBR296C |
| 26 | YBR297W |
| 27 | YBR298C |
| 28 | YBR301W |
| 29 | YCL051W |
| 30 | YCR005C |
| 31 | YCR072C |
| 32 | YCR107W |
| 33 | YDL022W |

TABLE 1-continued

| No. | Systematic gene name |
|---|---|
| 34 | YDL024C |
| 35 | YDL031W |
| 36 | YDL037C |
| 37 | YDL039C |
| 38 | YDL059C |
| 39 | YDL070W |
| 40 | YDL075W |
| 41 | YDL113C |
| 42 | YDL115C |
| 43 | YDL125C |
| 44 | YDL169C |
| 45 | YDL204W |
| 46 | YDL243C |
| 47 | YDR003W |
| 48 | YDR018C |
| 49 | YDR056C |
| 50 | YDR070C |
| 51 | YDR111C |
| 52 | YDR174W |
| 53 | YDR184C |
| 54 | YDR219C |
| 55 | YDR253C |
| 56 | YDR256C |
| 57 | YDR262W |
| 58 | YDR306C |
| 59 | YDR336W |
| 60 | YDR346C |
| 61 | YDR387C |
| 62 | YDR398W |
| 63 | YDR435C |
| 64 | YDR453C |
| 65 | YDR471W |
| 66 | YDR492W |
| 67 | YDR496C |
| 68 | YDR504C |
| 69 | YDR516C |
| 70 | YDR530C |
| 71 | YDR542W |
| 72 | YEL011W |
| 73 | YEL039C |
| 74 | YEL072W |
| 75 | YER020W |
| 76 | YER042W |
| 77 | YER053C |
| 78 | YER056C |
| 79 | YER065C |
| 80 | YER066W |
| 81 | YER067W |
| 82 | YER078C |
| 83 | YER079W |
| 84 | YER117W |
| 85 | YER150W |
| 86 | YFL014W |
| 87 | YFL030W |
| 88 | YFL055W |
| 89 | YFL056C |
| 90 | YFL057C |
| 91 | YFR014C |
| 92 | YFR015C |
| 93 | YFR017C |
| 94 | YFR053C |
| 95 | YGL029W |
| 96 | YGL033W |
| 97 | YGL045W |
| 98 | YGL075C |
| 99 | YGL122C |
| 100 | YGL135W |
| 101 | YGL179C |
| 102 | YGL184C |
| 103 | YGL255W |
| 104 | YGL261C |
| 105 | YGR008C |
| 106 | YGR043C |
| 107 | YGR053C |
| 108 | YGR088W |
| 109 | YGR102C |
| 110 | YGR154C |
| 111 | YGR197C |
| 112 | YGR222W |
| 113 | YGR223C |
| 114 | YGR251W |
| 115 | YGR256W |
| 116 | YGR262C |
| 117 | YGR286C |
| 118 | YGR294W |
| 119 | YHL016C |
| 120 | YHL021C |
| 121 | YHL036W |
| 122 | YHL046C |
| 123 | YHR066W |
| 124 | YHR087W |
| 125 | YHR138C |
| 126 | YHR139C |
| 127 | YHR141C |
| 128 | YHR146W |
| 129 | YIL036W |
| 130 | YIL045W |
| 131 | YIL069C |
| 132 | YIL077C |
| 133 | YIL107C |
| 134 | YIL136W |
| 135 | YIL143C |
| 136 | YIL153W |
| 137 | YJL132W |
| 138 | YJL155C |
| 139 | YJL223C |
| 140 | YJR085C |
| 141 | YJR155W |
| 142 | YKL026C |
| 143 | YKL070W |
| 144 | YKL071W |
| 145 | YKL078W |
| 146 | YKL087C |
| 147 | YKL089W |
| 148 | YKL090W |
| 149 | YKL091C |
| 150 | YKL094W |
| 151 | YKL103C |
| 152 | YKL125W |
| 153 | YKL150W |
| 154 | YKL151C |
| 155 | YKL162C |
| 156 | YKL187C |
| 157 | YKL224C |
| 158 | YKR049C |
| 159 | YKR075C |
| 160 | YKR077W |
| 161 | YKR100C |
| 162 | YLL055W |
| 163 | YLL056C |
| 164 | YLR009W |
| 165 | YLR145W |
| 166 | YLR149C |
| 167 | YLR164W |
| 168 | YLR251W |
| 169 | YLR252W |
| 170 | YLR266C |
| 171 | YLR311C |
| 172 | YLR312C |
| 173 | YLR327C |
| 174 | YLR413W |
| 175 | YLR421C |
| 176 | YML004C |
| 177 | YML128C |
| 178 | YML131W |
| 179 | YMR030W |
| 180 | YMR090W |
| 181 | YMR100W |
| 182 | YMR105C |
| 183 | YMR107W |
| 184 | YMR139W |
| 185 | YMR246W |

TABLE 1-continued

| No. | Systematic gene name |
|---|---|
| 186 | YMR255W |
| 187 | YMR258C |
| 188 | YMR262W |
| 189 | YMR271C |
| 190 | YMR316W |
| 191 | YMR320W |
| 192 | YMR322C |
| 193 | YNL011C |
| 194 | YNL024C |
| 195 | YNL112W |
| 196 | YNL117W |
| 197 | YNL124W |
| 198 | YNL141W |
| 199 | YNL142W |
| 200 | YNL178W |
| 201 | YNL194C |
| 202 | YNL195C |
| 203 | YNL213C |
| 204 | YNL244C |
| 205 | YNL331C |
| 206 | YNR039C |
| 207 | YNR051C |
| 208 | YNR053C |
| 209 | YNR071C |
| 210 | YNR075W |
| 211 | YNR076W |
| 212 | YOL002C |
| 213 | YOL016C |
| 214 | YOL084W |
| 215 | YOL101C |
| 216 | YOL108C |
| 217 | YOL116W |
| 218 | YOL124C |
| 219 | YOL127W |
| 220 | YOL132W |
| 221 | YOL153C |
| 222 | YOL154W |
| 223 | YOL161C |
| 224 | YOL162W |
| 225 | YOL163W |
| 226 | YOL165C |
| 227 | YOR019W |
| 228 | YOR031W |
| 229 | YOR043W |
| 230 | YOR095C |
| 231 | YOR292C |
| 232 | YOR298W |
| 233 | YOR391C |
| 234 | YOR394W |
| 235 | YPL004C |
| 236 | YPL014W |
| 237 | YPL015C |
| 238 | YPL043W |
| 239 | YPL054W |
| 240 | YPL093W |
| 241 | YPL107W |
| 242 | YPL122C |
| 243 | YPL149W |
| 244 | YPL171C |
| 245 | YPL186C |
| 246 | YPL223C |
| 247 | YPL224C |
| 248 | YPL245W |
| 249 | YPL250C |
| 250 | YPL280W |
| 251 | YPL281C |
| 252 | YPL282C |
| 253 | YPR045C |
| 254 | YPR061C |
| 255 | YPR086W |
| 256 | YPR121W |
| 257 | YPR143W |
| 258 | YPR160W |
| 259 | YPR200C |

In addition, the present invention relates to a DNA fragment having a cold-inducible promoter function, which comprises DNA described in the following (a) or (b):

(a) DNA existing in the non-translation region located upstream of the 5'-terminal side of a gene selected from the group consisting of genes of *Saccharomyces cerevisiae* described in Table 1, and comprising a deletion, substitution or addition of one or more nucleotides with respect to the DNA fragment having a cold-inducible promoter function; or (b) DNA existing in the non-translation region located upstream of the 5'-terminal side of a gene selected from the group consisting of genes of *Saccharomyces cerevisiae* described in Table 1, and hybridizing with a DNA fragment consisting of a nucleotide sequence complementary to the DNA fragment having a cold-inducible promoter function under stringent conditions.

Moreover, the present invention relates to a DNA fragment, which comprises a cis sequence of the following (a) or (b), and has a cold-inducible promoter function:

(a) DNA sequence A: GCTCATCG;
or (b) DNA sequence B: GAGATGAG.

Furthermore, the present invention relates to a DNA fragment having a cold-inducible promoter function, which comprises DNA described in the following (a) or (b):

(a) DNA having the above cis sequence, and comprising a deletion, substitution or addition of one or more nucleotides with respect to the DNA fragment having a cold-inducible promoter function; or (b) DNA having the above cis sequence, and hybridizing with a DNA fragment consisting of a nucleotide sequence complementary to the DNA fragment having a cold-inducible promoter function under stringent conditions.

Still further, the present invention relates to an expression vector comprising the above DNA fragment, or an expression vector characterized in that it comprises a foreign gene or foreign DNA fragment downstream of the above DNA fragment in the above expression vector.

Still further, the present invention relates to a transformant transformed with the above expression vector. An example of a host is yeast.

Still further, the present invention relates to a method for producing a protein or a method for regulating RNA production, which is characterized in that it comprises decreasing a culture temperature and culturing the transformant at the decreased temperature. An example of a culture temperature is 10° C. or lower.

The present invention will be described in detail below. The present application claims priority from Japanese Patent Application No. 2002-191383 filed on Jun. 28, 2002. This specification includes part or all of the contents as disclosed in the specification and/or drawings of the above Japanese Patent Application.

By identifying a cold-inducible gene of yeast, the DNA fragment of the present invention having a cold-inducible promoter function of yeast can be identified. Genes, the amount of mRNA of which is increased when the culture temperature is decreased from 30° C., an optimal culture temperature for yeast, to 10° C., are identified as cold-inducible genes. In order to completely capture these cold-inducible genes, approximately 5,800 genes are obtained by eliminating genes, whose preparation is difficult for reasons such as amplification or the like, from all genes (approximately 6,200) derived from *Saccharomyces cerevisiae*.

Thereafter, cDNA derived from each of the 5,800 genes is fixed on a slide glass, so as to prepare a DNA microarray (manufactured by DNA Chip Research Inc.). As RNA samples allowing to act on the DNA microarray, multiple RNA samples prepared by recovering a cell mass over time after decreasing the culture temperature of *Saccharomyces cerevisiae* from 30° C. to 10° C. and then extracting RNA from the recovered cell mass can be used. Using the thus prepared multiple samples, genes whose expression level increases immediately after shifting the culture temperature of *Saccharomyces cerevisiae* to a low temperature, and genes whose expression level gradually increases, can be identified. Using these RNA samples, the mRNA amount of each gene fixed on a DNA microarray is compared between before and after a low temperature treatment, so that a gene whose mRNA amount after the low temperature treatment is greater than the mRNA amount before the low temperature treatment can be identified as a cold-inducible gene. For example, a gene whose mRNA amount after a low temperature treatment is 3 times or more greater than the mRNA amount before the low temperature treatment can be identified as a cold-inducible gene. The thus identified 259 genes which are novel as a cold-inducible gene are shown in the following Table 2.

TABLE 2

| No. | Systematic gene name |
| --- | --- |
| 1 | YAL014C |
| 2 | YAL015C |
| 3 | YAL025C |
| 4 | YAL034C |
| 5 | YBL048W |
| 6 | YBL049W |
| 7 | YBL054W |
| 8 | YBL056W |
| 9 | YBL065W |
| 10 | YBL078C |
| 11 | YBR016W |
| 12 | YBR018C |
| 13 | YBR024W |
| 14 | YBR034C |
| 15 | YBR045C |
| 16 | YBR047W |
| 17 | YBR050C |
| 18 | YBR072W |
| 19 | YBR116C |
| 20 | YBR117C |
| 21 | YBR126C |
| 22 | YBR148W |
| 23 | YBR199W |
| 24 | YBR223C |
| 25 | YBR296C |
| 26 | YBR297W |
| 27 | YBR298C |
| 28 | YBR301W |
| 29 | YCL051W |
| 30 | YCR005C |
| 31 | YCR072C |
| 32 | YCR107W |
| 33 | YDL022W |
| 34 | YDL024C |
| 35 | YDL031W |
| 36 | YDL037C |
| 37 | YDL039C |
| 38 | YDL059C |
| 39 | YDL070W |
| 40 | YDL075W |
| 41 | YDL113C |
| 42 | YDL115C |
| 43 | YDL125C |
| 44 | YDL169C |
| 45 | YDL204W |
| 46 | YDL243C |
| 47 | YDR003W |
| 48 | YDR018C |
| 49 | YDR056C |
| 50 | YDR070C |
| 51 | YDR111C |
| 52 | YDR174W |
| 53 | YDR184C |
| 54 | YDR219C |
| 55 | YDR253C |
| 56 | YDR256C |
| 57 | YDR262W |
| 58 | YDR306C |
| 59 | YDR336W |
| 60 | YDR346C |
| 61 | YDR387C |
| 62 | YDR398W |
| 63 | YDR435C |
| 64 | YDR453C |
| 65 | YDR471W |
| 66 | YDR492W |
| 67 | YDR496C |
| 68 | YDR504C |
| 69 | YDR516C |
| 70 | YDR530C |
| 71 | YDR542W |
| 72 | YEL011W |
| 73 | YEL039C |
| 74 | YEL072W |
| 75 | YER020W |
| 76 | YER042W |
| 77 | YER053C |
| 78 | YER056C |
| 79 | YER065C |
| 80 | YER066W |
| 81 | YER067W |
| 82 | YER078C |
| 83 | YER079W |
| 84 | YER117W |
| 85 | YER150W |
| 86 | YFL014W |
| 87 | YFL030W |
| 88 | YFL055W |
| 89 | YFL056C |
| 90 | YFL057C |
| 91 | YFR014C |
| 92 | YFR015C |
| 93 | YFR017C |
| 94 | YFR053C |
| 95 | YGL029W |
| 96 | YGL033W |
| 97 | YGL045W |
| 98 | YGL075C |
| 99 | YGL122C |
| 100 | YGL135W |
| 101 | YGL179C |
| 102 | YGL184C |
| 103 | YGL255W |
| 104 | YGL261C |
| 105 | YGR008C |
| 106 | YGR043C |
| 107 | YGR053C |
| 108 | YGR088W |
| 109 | YGR102C |
| 110 | YGR154C |
| 111 | YGR197C |
| 112 | YGR222W |
| 113 | YGR223C |
| 114 | YGR251W |
| 115 | YGR256W |
| 116 | YGR262C |
| 117 | YGR286C |
| 118 | YGR294W |
| 119 | YHL016C |
| 120 | YHL021C |

TABLE 2-continued

| No. | Systematic gene name |
|---|---|
| 121 | YHL036W |
| 122 | YHL046C |
| 123 | YHR066W |
| 124 | YHR087W |
| 125 | YHR138C |
| 126 | YHR139C |
| 127 | YHR141C |
| 128 | YHR146W |
| 129 | YIL036W |
| 130 | YIL045W |
| 131 | YIL069C |
| 132 | YIL077C |
| 133 | YIL107C |
| 134 | YIL136W |
| 135 | YIL143C |
| 136 | YIL153W |
| 137 | YJL132W |
| 138 | YJL155C |
| 139 | YJL223C |
| 140 | YJR085C |
| 141 | YJR155W |
| 142 | YKL026C |
| 143 | YKL070W |
| 144 | YKL071W |
| 145 | YKL078W |
| 146 | YKL087C |
| 147 | YKL089W |
| 148 | YKL090W |
| 149 | YKL091C |
| 150 | YKL094W |
| 151 | YKL103C |
| 152 | YKL125W |
| 153 | YKL150W |
| 154 | YKL151C |
| 155 | YKL162C |
| 156 | YKL187C |
| 157 | YKL224C |
| 158 | YKR049C |
| 159 | YKR075C |
| 160 | YKR077W |
| 161 | YKR100C |
| 162 | YLL055W |
| 163 | YLL056C |
| 164 | YLR009W |
| 165 | YLR145W |
| 166 | YLR149C |
| 167 | YLR164W |
| 168 | YLR251W |
| 169 | YLR252W |
| 170 | YLR266C |
| 171 | YLR311C |
| 172 | YLR312C |
| 173 | YLR327C |
| 174 | YLR413W |
| 175 | YLR421C |
| 176 | YML004C |
| 177 | YML128C |
| 178 | YML131W |
| 179 | YMR030W |
| 180 | YMR090W |
| 181 | YMR100W |
| 182 | YMR105C |
| 183 | YMR107W |
| 184 | YMR139W |
| 185 | YMR246W |
| 186 | YMR255W |
| 187 | YMR258C |
| 188 | YMR262W |
| 189 | YMR271C |
| 190 | YMR316W |
| 191 | YMR320W |
| 192 | YMR322C |
| 193 | YNL011C |
| 194 | YNL024C |
| 195 | YNL112W |
| 196 | YNL117W |
| 197 | YNL124W |
| 198 | YNL141W |
| 199 | YNL142W |
| 200 | YNL178W |
| 201 | YNL194C |
| 202 | YNL195C |
| 203 | YNL213C |
| 204 | YNL244C |
| 205 | YNL331C |
| 206 | YNR039C |
| 207 | YNR051C |
| 208 | YNR053C |
| 209 | YNR071C |
| 210 | YNR075W |
| 211 | YNR076W |
| 212 | YOL002C |
| 213 | YOL016C |
| 214 | YOL084W |
| 215 | YOL101C |
| 216 | YOL108C |
| 217 | YOL116W |
| 218 | YOL124C |
| 219 | YOL127W |
| 220 | YOL132W |
| 221 | YOL153C |
| 222 | YOL154W |
| 223 | YOL161C |
| 224 | YOL162W |
| 225 | YOL163W |
| 226 | YOL165C |
| 227 | YOR019W |
| 228 | YOR031W |
| 229 | YOR043W |
| 230 | YOR095C |
| 231 | YOR292C |
| 232 | YOR298W |
| 233 | YOR391C |
| 234 | YOR394W |
| 235 | YPL004C |
| 236 | YPL014W |
| 237 | YPL015C |
| 238 | YPL043W |
| 239 | YPL054W |
| 240 | YPL093W |
| 241 | YPL107W |
| 242 | YPL122C |
| 243 | YPL149W |
| 244 | YPL171C |
| 245 | YPL186C |
| 246 | YPL223C |
| 247 | YPL224C |
| 248 | YPL245W |
| 249 | YPL250C |
| 250 | YPL280W |
| 251 | YPL281C |
| 252 | YPL282C |
| 253 | YPR045C |
| 254 | YPR061C |
| 255 | YPR086W |
| 256 | YPR121W |
| 257 | YPR143W |
| 258 | YPR160W |
| 259 | YPR200C |

The DNA fragment of the present invention exists in the non-translation region located upstream of the 5'-terminal side of a gene selected from the group consisting of genes of *Saccharomyces cerevisiae* described in the above Table 2, and functions as a cold-inducible promoter.

Table 2 shows numbers from 1 to 259 imparted to 259 genes in association with systematic gene names thereof. These systematic gene names correspond to the names registered as systematic names in yeast genome database (*Saccharomyces cerevisiae* genome database.) Accordingly, the genes of *Saccharomyces cerevisiae* described in the above Table 2 can easily be specified by using such a systematic gene name as a key and searching for the systematic name through the yeast genome database. Moreover, the nucleotide sequences of the genes of *Saccharomyces cerevisiae* described in Table 2 can be obtained by searching through the yeast genome database. Furthermore, other types of information regarding the genes of *Saccharomyces cerevisiae* described in Table 2 can also be obtained by searching though the yeast genome database.

The term "a cold-inducible promoter" means a promoter exhibiting higher promoter activity at a temperature lower than the optimal culture temperature for yeast as compared to the promoter activity obtained at the optimal culture temperature for yeast. More specifically, such a cold-inducible promoter exhibits 3 times or more higher promoter activity at a temperature lower than the optimal culture temperature for yeast as compared to the promoter activity obtained at the optimal culture temperature for yeast. Herein, the optimal culture temperature for yeast is approximately 30° C. In addition, the term "a temperature lower than the optimal culture temperature for yeast" means a temperature lower than 30° C., and for example, approximately 10° C. However, if the above temperature is a temperature of 20° C. or lower, and preferably 15° C. or lower, it is not limited to approximately 10° C.

Promoter activity can be measured according to conventional methods. For example, an expression vector, in which a reporter gene is ligated downstream of a promoter such that the gene can be expressed, is constructed. Subsequently, a suitable host (e.g. yeast) is transformed with the expression vector. The obtained transformant is cultured under certain conditions, and the expression level of the reporter gene can be assayed at a level of mRNA or protein, so as to measure promoter activity under the above-described conditions.

The term "non-translation region located upstream of the 5'-terminal side of a gene" means a region, which exists on the 5'-terminal side of the coding strand of a gene specified as stated above and is not translated into a protein. In other words, such a non-translation region means a region that is not included in what is called ORF (open reading frame).

The non-translation region located upstream of 5'-terminal side of a certain gene (hereinafter referred to as a target gene) can specifically be identified using the yeast genome database. That is to say, first, a search is performed through the yeast genome database using the systematic gene name of a target gene as a key. As a result of the search, various types of information regarding the target gene are obtained. Using various types of information, the position of the target gene on a chromosome is determined. Thereafter, on the basis of the position of the target gene on a chromosome, a gene located upstream of the 5'-terminal side of the target gene (referred to as a 5' upstream adjacent gene) is specified from the chromosome map registered in the yeast genome database. A region sandwiched between the thus specified target gene and 5' upstream adjacent gene is a region that is neither translated into a protein, nor contains ORF. Thus, the region sandwiched between the target gene and 5' upstream adjacent gene can be specified by the above-described processes as a non-translation region on the 5'-terminal side of the target gene.

The nucleotide sequence of the thus specified non-translation region on the 5'-terminal side of the target gene can be obtained by searching information regarding total nucleotide sequences of yeast genome registered in the yeast genome database. In addition, the specified non-translation region on the 5'-terminal side of the target gene can easily be obtained by performing PCR using the genome extracted form yeast as a template and also using primers complementary to the nucleotide sequences at both termini of the above region consisting of approximately 20 nucleotides.

The DNA fragment of the present invention may be either the entire non-translation region on the 5'-terminal side, or a portion of the non-translation region on 5'-terminal side as long as it has a function as a cold-inducible promoter.

Moreover, the DNA fragment of the present invention may be a DNA fragment, which comprises DNA comprising a deletion, substitution or addition of one or several (for example, 1 to 10, or 1 to 5) nucleotides with respect to the above DNA fragment and has a cold-inducible promoter function.

Furthermore, in the DNA fragment of the present invention included is a DNA fragment, which hybridizes with a DNA fragment consisting of a nucleotide sequence complementary to the above DNA fragment under stringent conditions and has a cold-inducible promoter function.

Herein, when probe DNA labeled with phosphorus-32 is used, the term "stringent conditions" is used to mean hybridization performed in a hybridization solution consisting of 5×SSC (0.75 M NaCl, 0.75 M sodium citrate), 5× Denhardt's reagent (0.1% ficoll, 0.1% polyvinylpyrrolidone, 0.1% bovine serum albumin), and 0.1% sodium dodecyl sulfate (SDS), at a temperature between 45° C. and 65° C., and preferably between 55° C. and 65° C. In addition, in a washing step, washing is performed in a washing solution consisting of 2×SSC and 0.1% SDS at a temperature between 45° C. and 55° C., and more preferably, washing is performed in a washing solution consisting of 0.1×SSC and 0.1% SDS at a temperature between 45° C. and 55° C. When probe DNA labeled with an enzyme using an AlkPhos direct labeling module kit (Amersham Biotech) is used, hybridization is carried out in a hybridization solution (containing 0.5 M NaCl and a 4% blocking reagent), the composition of which is described in a manual attached with the kit, at a temperature between 55° C. and 75° C. In addition, in a washing step, washing is performed in a first washing solution (containing 2 M urea) described in the manual attached with the kit at a temperature between 55° C. and 75° C., and then in a second washing solution at room temperature. Furthermore, other detection methods may also be applied. When other detection methods are applied, standard conditions for the applied detection method may be used.

The DNA fragment of the present invention may be a DNA fragment, which comprises DNA described in the following (a) or (b) and has a cold-inducible promoter function:

(a) DNA sequence A:       GCTCATCG;
or (b) DNA sequence B:       GAGATGAG.

The DNAs described in the above (a) and (b) are sequences (referred to as cis sequences) that are common in the non-translation regions located upstream of the 5'-terminal sides of genes exhibiting cold inducibility at an early stage, which are identified by the above-described method using the above-described DNA microarray. For example, regarding genes exhibiting cold inducibility at an early stage, the culture temperature is first decreased to 10° C. Then, 15 minutes later, genes whose signal is 2 times or more increased can be identified as genes exhibiting cold inducibility at an early stage. The identified 41 genes are shown in the following Table 3.

TABLE 3

| No. | Systematic gene name |
|---|---|
| 1 | YDL039C |
| 2 | YNL141W |
| 3 | YDL037C |
| 4 | YKR075C |
| 5 | YER056C |
| 6 | YOL124C |
| 7 | YDR492W |
| 8 | YLR413W |
| 9 | YCR072C |
| 10 | YOR095C |
| 11 | YNL175C |
| 12 | YDR398W |
| 13 | YGR283C |
| 14 | YBR296C |
| 15 | YDR184C |
| 16 | YOR338W |
| 17 | YAL025C |
| 18 | YOR063W |
| 19 | YIL096C |
| 20 | YER127W |
| 21 | YBL042C |
| 22 | YDL063C |
| 23 | YOR360C |
| 24 | YHR196W |
| 25 | YNL065W |
| 26 | YHR066W |
| 27 | YLR407W |
| 28 | YOR101W |
| 29 | YNL112W |
| 30 | YGR159C |
| 31 | YGL055W |
| 32 | YNR053C |
| 33 | YPL093W |
| 34 | YHR170W |
| 35 | YHR148W |
| 36 | YBR034C |
| 37 | YOL010W |
| 38 | YKL078W |
| 39 | YMR290C |
| 40 | YDR101C |
| 41 | YBL054W |

Table 3 shows numbers from 1 to 41 imparted to 41 genes in association with systematic gene names thereof As in the case of Table 2, these systematic gene names correspond to the names registered as systematic names in the above-described yeast genome database.

Subsequently, using Gene Spring (Silicon Genetics), cis sequences existing between the ORF and 600 bp upstream of individual genes are searched. As a result, common DNA sequences existing in some of these genes can be obtained. Specifically, the above DNA sequence A is a common cis sequence that can be found in YNL112W, YGR159C, YGL055W, YNR053C, YPL093W, YHR170W, and YHR148W (which correspond to Nos. 29 to 35 in Table 3), and the above DNA sequence B is a common cis sequence that can be found in YBR034C, YOL010W, YKL078W, YMR290C, YDR101C, and YBL054W (which correspond to Nos. 36 to 41 in Table 3).

Further, the above DNA fragment may be a DNA fragment, which comprises DNA comprising a deletion, substitution or addition of one or several nucleotides (for example, 1 to 3) with respect to the above DNA fragment, and has a cold-inducible promoter function.

Furthermore, a DNA fragment comprising DNA hybridizing with a DNA fragment consisting of a nucleotide sequence complementary to the above DNA fragment under stringent conditions and having a cold-inducible promoter function may also be included in the DNA fragment of the present invention.

Herein, when probe DNA labeled with phosphorus-32 is used, the term "stringent conditions" is used to mean hybridization performed in a hybridization solution consisting of 5×SSC (0.75 M NaCl, 0.75 M sodium citrate), 5× Denhardt's reagent (0.1% ficoll, 0.1% polyvinylpyrrolidone, 0.1% bovine serum albumin), and 0.1% sodium dodecyl sulfate (SDS), at a temperature between 45° C. and 65° C., and preferably between 55° C. and 65° C. In addition, in a washing step, washing is performed in a washing solution consisting of 2×SSC and 0.1% SDS at a temperature between 45° C. and 55° C., and more preferably, washing is performed in a washing solution consisting of 0.1×SSC and 0.1% SDS at a temperature between 45° C. and 55° C. When probe DNA labeled with an enzyme using an AlkPhos direct labeling module kit (Amersham Biotech) is used, hybridization is carried out in a hybridization solution (containing 0.5 M NaCl and a 4% blocking reagent), the composition of which is described in a manual attached with the kit, at a temperature between 55° C. and 75° C. In addition, in a washing step, washing is performed in a first washing solution (containing 2 M urea) described in a manual attached with the kit at a temperature between 55° C. and 75° C., and then in a second washing solution at room temperature. Furthermore, other detection methods may also be applied. When other detection methods are applied, standard conditions for the applied detection method may be used.

Once the nucleotide sequence of the DNA fragment of the present invention is established, then the DNA fragment of the present invention can be obtained by chemical synthesis, by performing PCR using the cloned probe as a template, or by hybridization of a DNA fragment having the above nucleotide sequence as a probe. Moreover, even in the case of a mutant of the DNA fragment of the present invention, a site-directed mutagenesis or other techniques can be applied, so as to synthesize a fragment having the same functions as those of a DNA fragment before mutation.

In order to introduce mutation into the DNA fragment of the present invention, known methods such as Kunkel method or Gapped duplex method, or methods equivalent thereto, can be applied. For example, mutation can be introduced by using a kit for introducing mutation (e.g. Mutant-K (manufactured by Takara) or Mutant G (manufactured by Takara)) using the site-directed mutagenesis, or by using a series of LA PCR in vitro Mutagenesis kits manufactured by Takara.

The expression vector of the present invention can be obtained by inserting the DNA fragment of the present invention into a suitable vector. A vector into which the DNA fragment of the present invention is inserted is not particularly limited, as long as it can replicate itself in a host. Examples of such a vector may include a plasmid, a shuttle vector, and a helper plasmid. When a vector has no self-replicating ability, a DNA fragment, which can replicate itself when it is inserted into the chromosome of a host, may be used.

Examples of plasmid DNA may include plasmids derived from *Escherichia coli* (e.g. pBR322, pBR325, pUC118, pUC119, pUC18, pUC19, and pBluescript), plasmids derived from *Bacillus subtilis* (e.g. pUB110 and pTP5), and plasmids derived from yeast (e.g. YEp system such as YEp13, and YCp system such as YCp50). Examples of phage DNA may include λ phages (e.g. Charon 4A, Charon 21A, EMBL 3, EMBL 4, λ gt10, λ gt11, and λ ZAP).

Moreover, animal viruses such as retrovirus or vaccinia virus, and insect viruses such as baculovirus, may also be used as viral vectors.

In order to insert the DNA fragment of the present invention into a vector, a method comprising, first cleaving the purified DNA with suitable restriction enzymes, and then inserting the obtained DNA portion into a restriction site or multicloning site of suitable vector DNA, and ligating it to the vector, is applied. Otherwise, it may also be possible that both vector and the DNA fragment of the present invention be allowed to have a portion of homologous regions, and that both be ligated by the in vitro method using PCR and the like, or by the in vivo method using yeast and the like.

The expression vector of the present invention may further comprise a foreign gene or foreign DNA fragment, which is inserted downstream of the DNA fragment of the present invention. A method of inserting such a foreign gene or foreign DNA fragment into a vector is the same as the method of inserting the DNA fragment of the present invention into a vector.

Any protein or peptide may be used as such a foreign gene located downstream of the DNA fragment of the present invention in the expression vector of the present invention. An example may be a protein that is particularly suitable for production at a low temperature. More specifically, examples of such a protein may include an antifreeze protein functioning at a low temperature, a cold-active enzyme that is thermolabile and is likely to denature due to heat, and a fluorescent protein GFP. Furthermore, examples of a foreign DNA fragment located downstream of the DNA fragment of the present invention may include antisense RNA and ribozyme, wherein RNA functions by itself.

The transformant of the present invention can be obtained by introducing the expression vector of the present invention into a host. A host is not particularly limited herein, as long as it can allow a promoter and a foreign gene to express. In the present invention, an example of the host may be yeast. Examples of such yeast may include *Saccharomyces cerevisiae*, experimental yeast, brewer's yeast, edible yeast, and industrial yeast.

A method of introducing the expression vector of the present invention into yeast is not particularly limited, as long as it is a method of introducing DNA into yeast. Examples of such a method may include electroporation, the spheroplast method, and the lithium acetate method. In addition, it may also be a yeast transformation method, which involves substitution or insertion into a chromosome, using a vector such as YIp system or a DNA sequence homologous to a certain region in a chromosome. Furthermore, any methods described in common experimental manuals or scientific papers may be applied as methods of introducing the expression vector of the present invention into a yeast cell.

The expression vector of the present invention is not only introduced into the aforementioned yeast hosts, but it can be also introduced into bacteria belonging to the genus *Escherichia* such as *Escherichia coli*, the genus *Bacillus* such as *Bacillus subtilis*, or the genus *Pseudomonas* such as *Pseudomonas putida*, animal cells such as COS cells, insect cells such as Sf9, or plants belonging to *Brassicaceae*, so as to obtain a transformant. When a bacterium is used as a host, it is preferable that the expression vector of the present invention be able to self-replicate in the bacterium, and also that it be composed of the DNA fragment of the present invention, a ribosome-binding sequence, a gene of interest, and a transcription termination sequence. In addition, a gene regulating a promoter may also be comprised in the expression vector.

A method of introducing the expression vector of the present invention into a bacterium is not particularly limited, as long as it is a method of introducing DNA into a bacterium. Examples of such a method may include a method of using calcium ions and electroporation.

When an animal cell is used as a host, a monkey cell COS-7, Vero, a Chinese hamster ovary cell (CHO cell), a mouse L cell, or the like is used. Examples of a method of introducing the expression vector of the present invention into an animal cell may include electroporation, the calcium phosphate method, and lipofection.

When an insect cell is used as a host, an Sf9 cell or the like is used. Examples of a method of introducing the expression vector of the present invention into an insect cell may include the calcium phosphate method, lipofection, and electroporation.

When a plant is used as a host, a plant body as a whole, a plant organ (e.g. a leaf, a petal, a stem, a root, and a seed), a plant tissue (e.g. epidermis, phloem, parenchyma, xylem, and vascular bundle), a plant cultured cell, or the like is used. Examples of a method of introducing the expression vector of the present invention into a plant may include electroporation, the *Agrobacterium* method, particle gun, and the PEG method.

Incorporation of a gene into a host can be confirmed by PCR, Southern hybridization, Northern hybridization, and other methods. For example, DNA is prepared from a transformant, DNA-specific primers are designed, and PCR is then carried out. Thereafter, the amplified product is subjected to agarose gel electrophoresis, polyacrylamide gel electrophoresis, capillary electrophoresis, etc., followed by staining with ethidium bromide, SYBR Green solution, or the like. Thereafter, the amplified product is detected as a single band, so as to confirm that transformation has been carried out. Also, PCR can be carried out using primers that have previously been labeled with fluorescent dye or the like, so as to detect an amplified product. Further, a method of binding an amplified product to a solid phase such as a microplate, and then confirming the amplified product by a fluorescent or enzyme reaction may also be adopted.

The method of the present invention for producing a protein comprises: introducing into a host an expression vector comprising the DNA fragment of the present invention and a foreign gene ligated downstream of the above DNA fragment, so as to prepare a transformant; and decreasing a culture temperature and culturing the transformant at the decreased temperature, so as to produce a protein encoded by the foreign gene located downstream thereof. An example of such a culture temperature may be 10° C. or lower. Since, for example, among cold-active enzymes or antifreeze proteins which some organisms living in a low temperature area have, these cold-active enzymes or antifreeze proteins can be extremely thermolabile, they may be denatured when they are produced at an ordinary temperature. In such a case, an expression vector, which comprises a gene encoding the aforementioned cold-active enzyme or antifreeze protein that is ligated downstream of the cold-inducible promoter of the present invention, is introduced into yeast, and the temperature in this system is decreased from approximately 30° C. as an optimal culture temperature for yeast to a lower temperature (for example, 10° C.), so that the amount of mRNA corresponding to the gene ligated downstream of the DNA fragment of the present invention can be increased and that an expression system for efficiently expressing an active protein can be constructed.

When a protein (enzyme) to be produced causes cell damage, such as the case of protease, since it inhibits the growth of a recombinant, it is extremely difficult to produce such a protein (enzyme). In this case, according to the protein production method of the present invention, a recombinant is first allowed to grow, while the production amount of a foreign gene product is limited at an optimal culture temperature (approximately 30° C.). Thereafter, at the time when a sufficient amount of cell mass is obtained, the temperature can be decreased, thereby inducibly producing a foreign gene product while suppressing cytotoxicity. Moreover, with regard to a fluorescent protein GFP that has frequently been used for kinetic analysis of intracellular proteins or biomonitoring in recent years, it has been known that when the protein is produced in a recombinant, it requires a maturation process of changing its structure into a protein structure for emitting fluorescence. It is considered that this maturation process is promoted at a low temperature. As a matter of fact, when the protein is produced at a temperature lower than the ordinary culture temperature, a higher amount of fluorescence can be obtained (Matsuzaki et al., a supplementary volume of *Jikken Igaku, post genome jidai no jikken koza* 3, "GFP to bioimaging," Yodosha Co., Ltd., (2000) pp. 31-37). Thus, the protein production method of the present invention enables biomonitoring whereby GFP is used at higher sensitivity.

Moreover, the method of the present invention for regulating RNA production comprises: preparing an expression vector comprising the DNA fragment of the present invention and a foreign DNA fragment ligated downstream of the above DNA fragment; introducing the expression vector into a host, so as to prepare a transformant; and decreasing a culture temperature and culturing the transformant at the decreased temperature, so that RNA production can be regulated by the foreign DNA fragment located downstream thereof. An example of such a culture temperature may be 10° C. or lower. For example, an expression vector, which comprises the cold-inducible promoter of the present invention and a gene encoding antisense RNA to a specific gene ligated downstream of the above promoter, is introduced into yeast, and the temperature in this system is decreased from approximately 30° C. as an optimal culture temperature for yeast to a lower temperature (for example, 10° C.), so that the amount of antisense RNA corresponding to the gene ligated downstream of the DNA fragment of the present invention can be increased and that the expression of the specific gene can be regulated.

Figure 13:
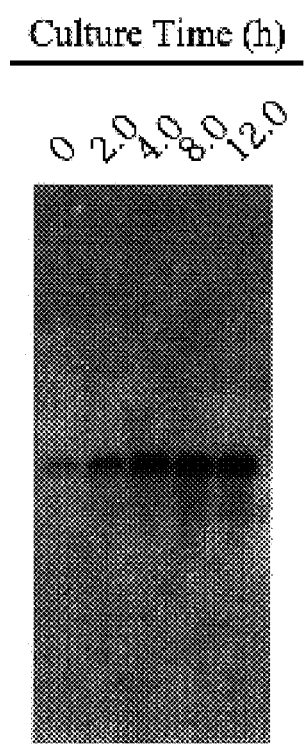
Figure 14:
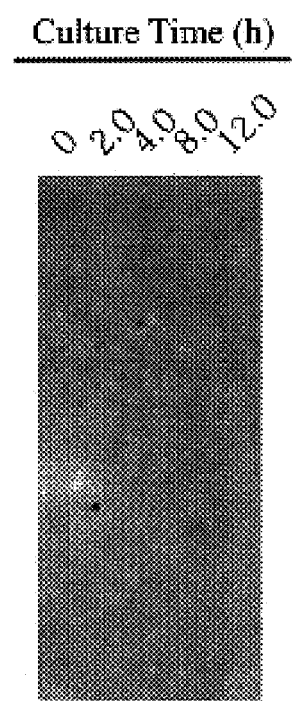
Figure 15:
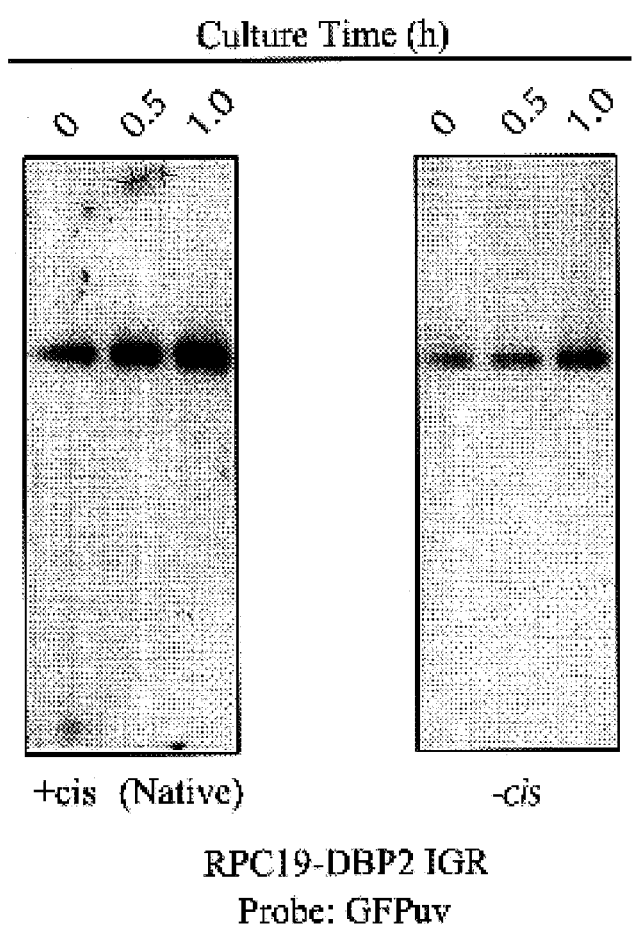
Figure 16:
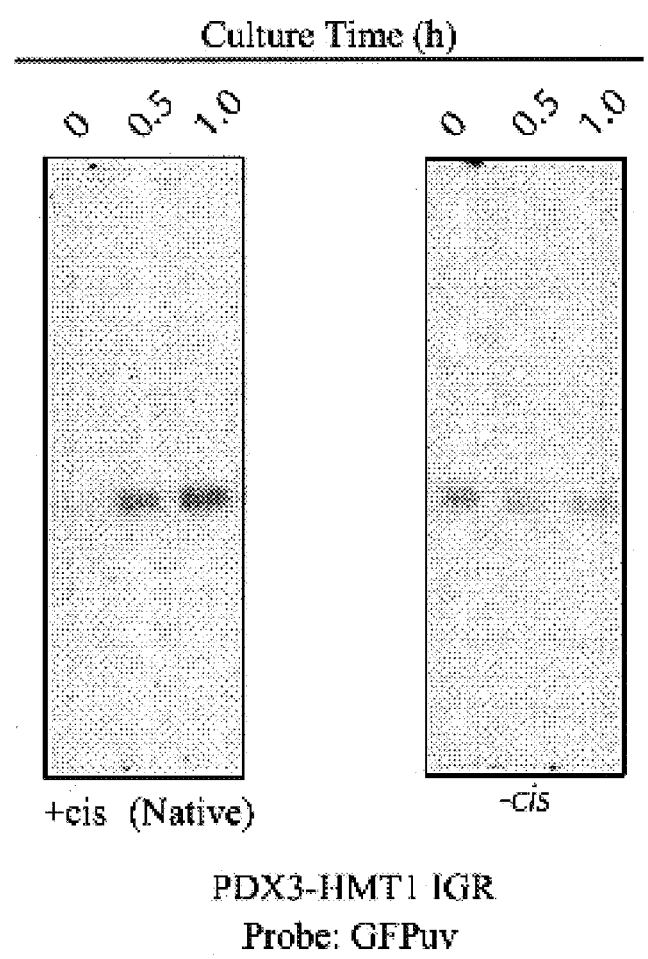
Figure 17:
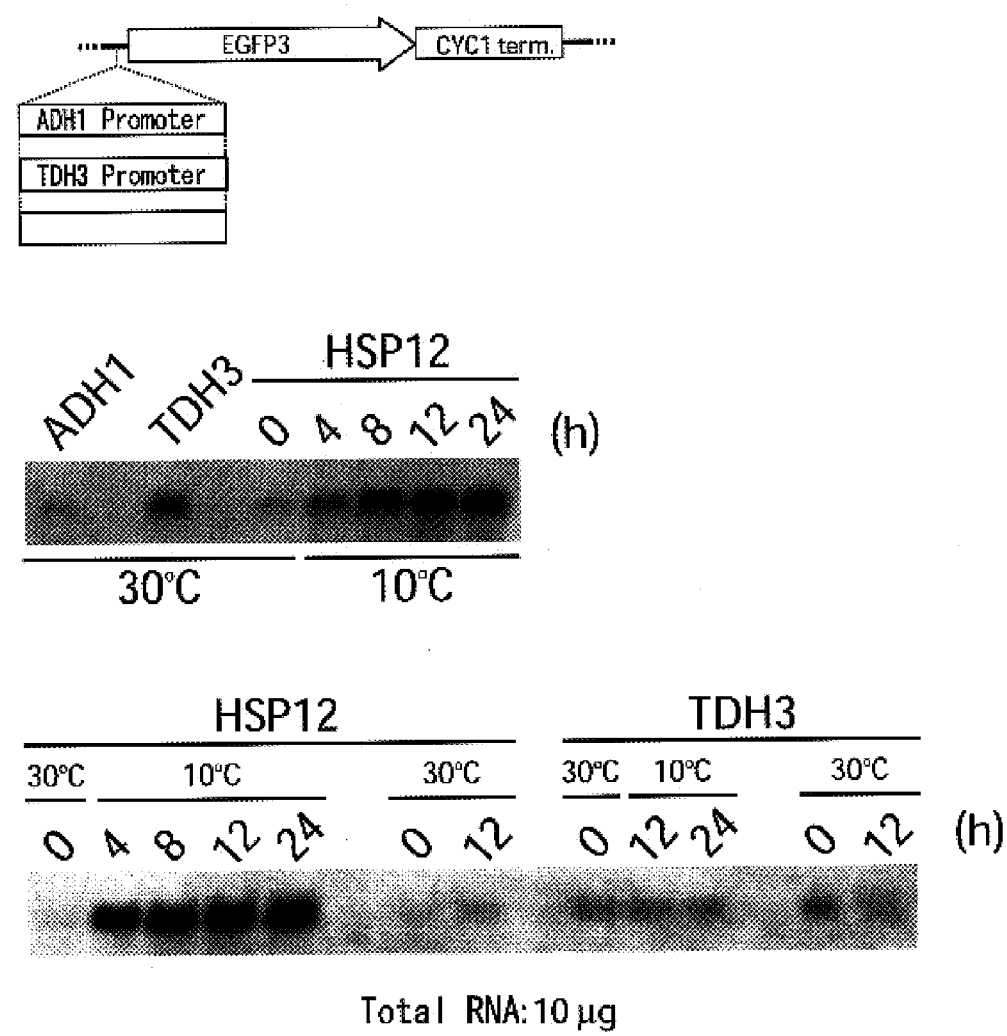
Figure 18:
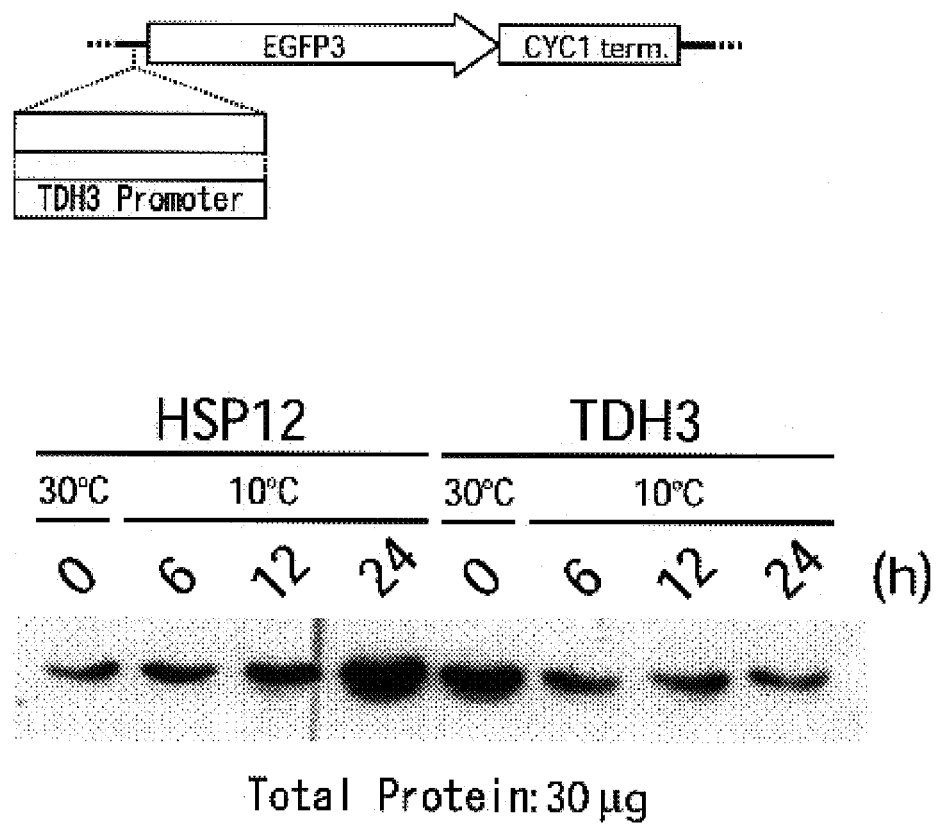
Figure 19:
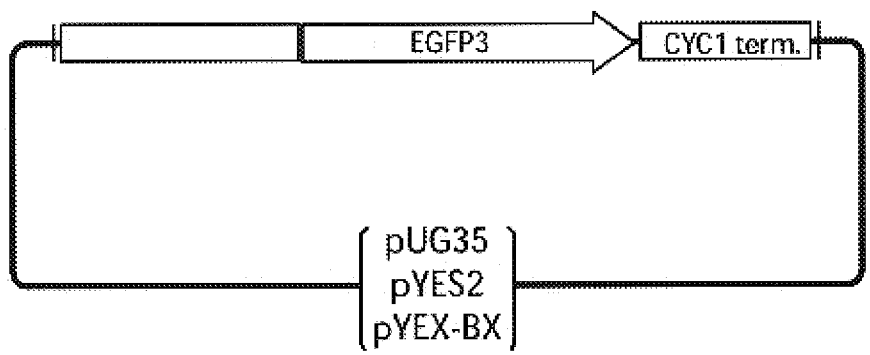
Figure 19:
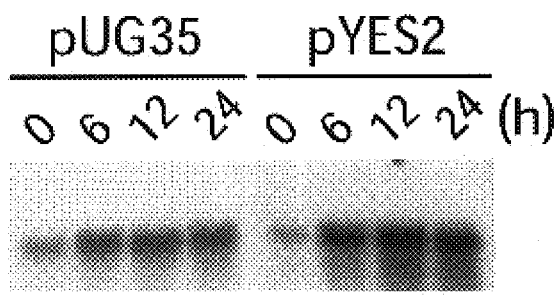
Figure 19:
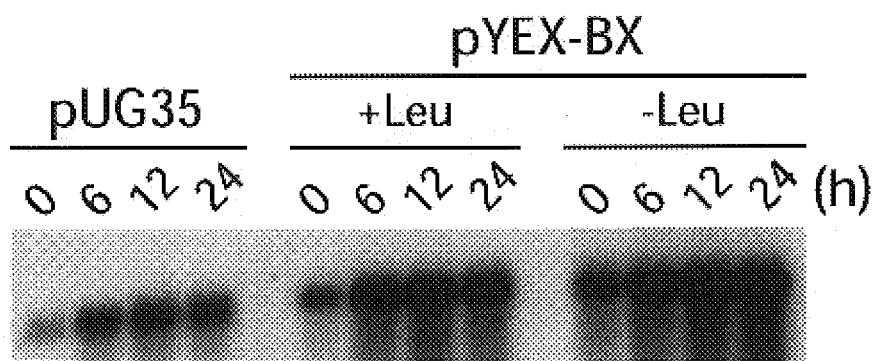
Figure 20:
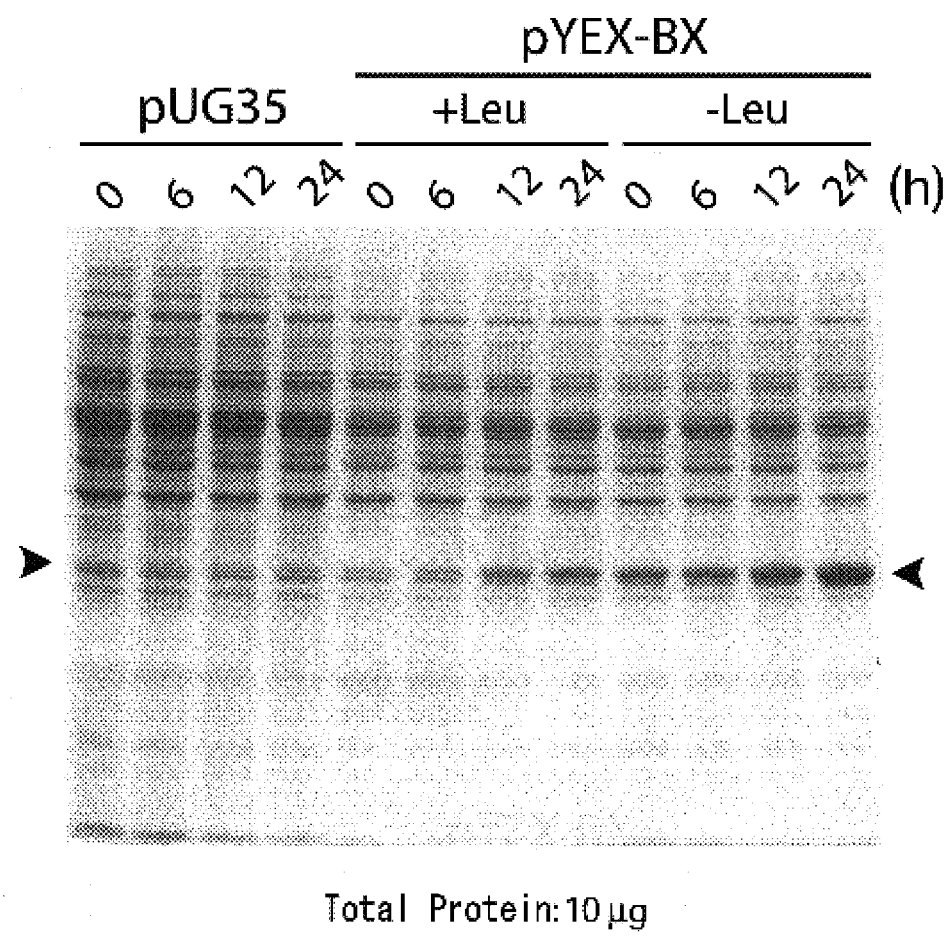
Figure 21:
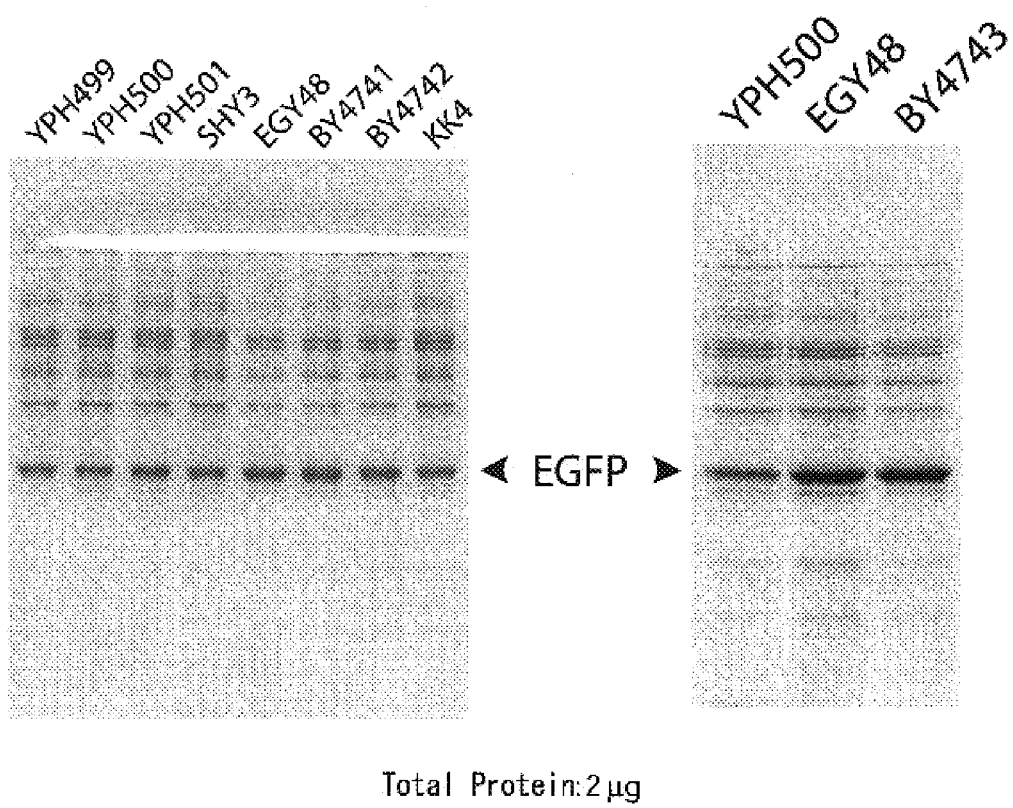
Figure 22:
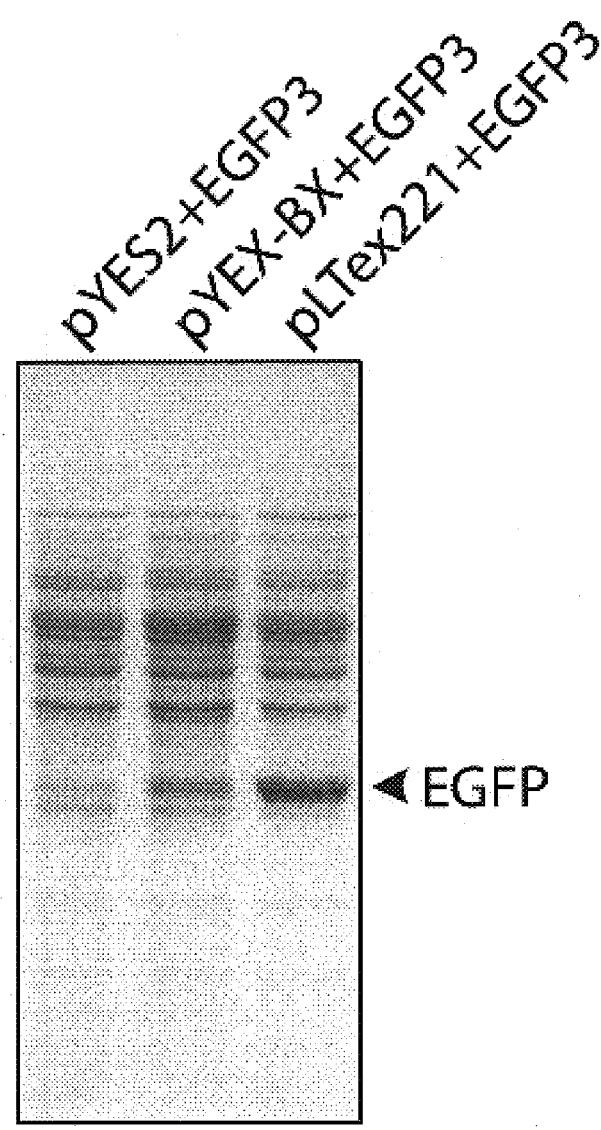
Figure 23:
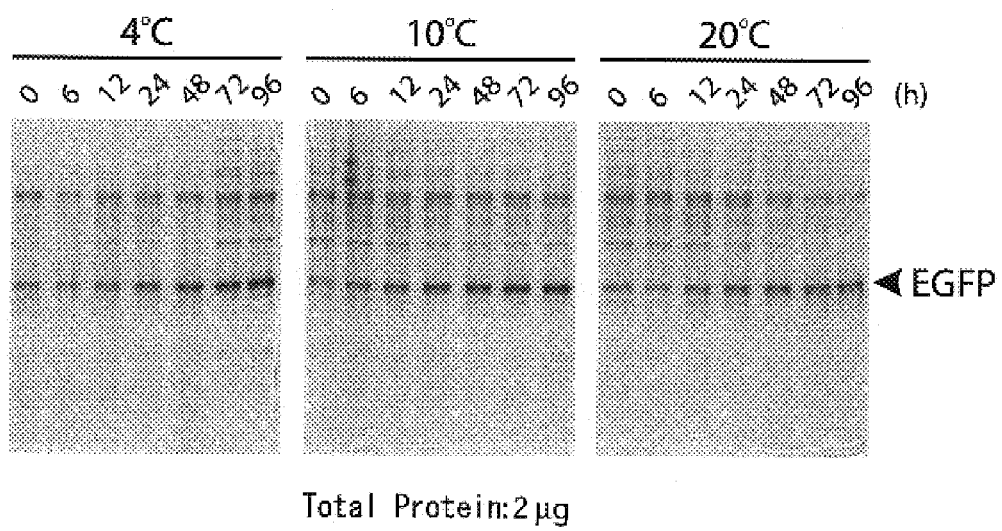
Figure 24:
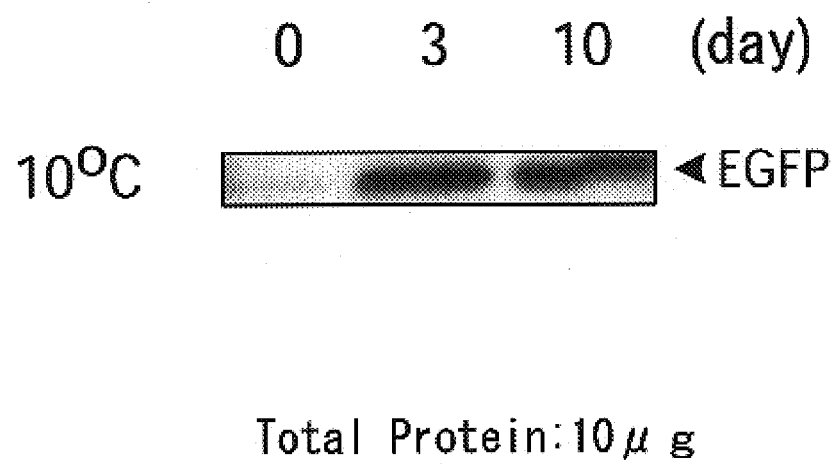
Figure 25:
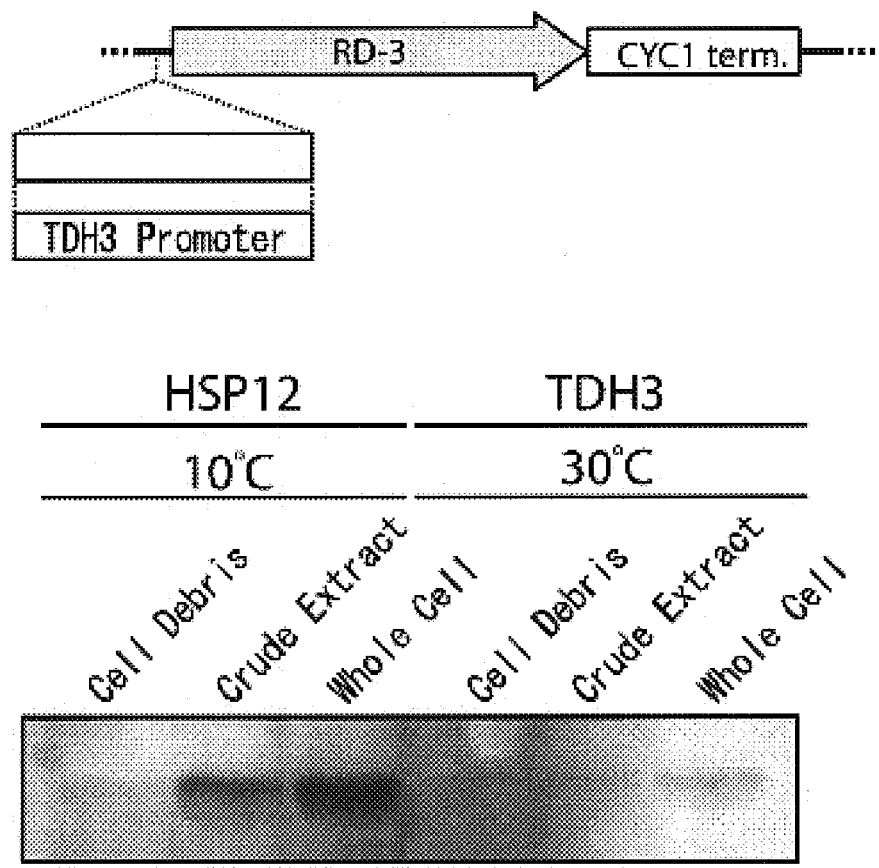
Figure 26:

The culture time after a low temperature treatment is shown at the top. The amount of mRNA is represented by the density and size of dots in each lane;

FIG. 13 shows the results of Northern blotting analysis showing a change in the amount of EGFP mRNA obtained when a DNA fragment having an HSP12 promoter function is ligated to EGFP DNA and when the culture temperature is decreased from 30° C. to 10° C. The culture time after a low temperature treatment is shown at the top. The amount of mRNA is represented by the density and size of dots in each lane;

FIG. 14 shows the results of Northern blotting analysis showing a change in the amount of EGFP mRNA obtained when a DNA fragment having an HSP12 promoter function is ligated in the direction opposite to EGFP DNA and when the culture temperature is decreased from 30° C. to 10° C. The culture time after a low temperature treatment is shown at the top. The amount of mRNA is represented by the density and size of dots in each lane;

FIG. 15 shows the results of Northern blotting analysis showing a change in the amount of EGFP mRNA, which is obtained, when a DNA fragment having a modified DBP2 promoter function (right) obtained by removing a DNA sequence A (GCTCATCG) from a DNA fragment having a DBP2 promoter function comprising the above DNA sequence A and a native DNA fragment having a DBP2 promoter function (left) are used, and when the culture temperature is decreased from 30° C. to 10° C. The culture time after a low temperature treatment is shown at the top. The amount of mRNA is represented by the density and size of dots in each lane;

FIG. 16 shows the results of Northern blotting analysis showing a change in the amount of EGFP mRNA, which is obtained, when a DNA fragment having a modified HMT1 promoter function (right) obtained by removing a DNA sequence B (GAGATGAG) from a DNA fragment having an HMT1 promoter function comprising the above DNA sequence B and a native DNA fragment having a HMT1 promoter function (left) are used, and when the culture temperature is decreased from 30° C. to 10° C. The culture time after a low temperature treatment is shown at the top. The amount of mRNA is represented by the density and size of dots in each lane;

FIG. 17 shows, in the upper case, a plasmid construct comprising an ADH1 promoter, a TDH3 promoter, or a DNA fragment having an HSP12 cold-inducible promoter function, and in the middle and lower cases, the results of Northern blotting analysis, which is performed to compare the transcriptional activity of a DNA fragment having an HSP12 cold-inducible promoter function with the transcriptional activities of an ADH1 promoter and a TDH3 promoter in yeast. The amount of EGFP mRNA is represented by the density and size of dots in each lane;

FIG. 18 shows, in the upper case, a plasmid construct comprising a TDH3 promoter or a DNA fragment having an HSP12 cold-inducible promoter function, and in the lower case, the results of Western blotting analysis, which is performed to compare the protein-producing ability of a DNA fragment having an HSP12 cold-inducible promoter function with the protein-producing ability of a TDH3 promoter in yeast. The amount of an EGFP protein is represented by the density and size of dots in each lane;

FIG. 19 shows, in the upper case, an expression plasmid construct, which is obtained by inserting an expression cassette comprising a DNA fragment having an HSP12 cold-inducible promoter function, the ORF of EGFP, and a CYC1 terminator, into pUG35 having a centromere as a replication origin, pYES2 having 2 µ as a replication origin, or pYEX-BX having 2 µ as a replication origin and having a weak leucine synthetase gene (leu2-d), from each of which an original promoter has been removed, and in the middle and lower cases, the results of Northern blotting analysis showing the fact that the ability of the transcriptional activation of a DNA fragment having an HSP12 cold-inducible promoter function does not depend on the structure of a plasmid in itself. The amount of EGFP mRNA is represented by the density and size of dots in each lane;

FIG. 20 shows the results of SDS-PAGE analysis showing the fact that the protein-producing ability of a DNA fragment having an HSP12 cold-inducible promoter function does not depend on the structure of a plasmid in itself The amount of an EGFP protein is represented by the density and size of a band indicated with an arrow in each lane;

FIG. 21 shows the results of SDS-PAGE analysis showing the fact that the protein-producing ability of a DNA fragment having an HSP12 cold-inducible promoter function does not depend on the type of yeast strain *Saccharomyces cerevisiae*. The amount of an EGFP protein is represented by the density and size of a band indicated with an arrow in each lane;

FIG. 22 shows the results of SDS-PAGE analysis showing the fact that the protein-producing ability of an expression vector comprising a DNA fragment having an HSP12 cold-inducible promoter function is more excellent than that of the existing expression vector of yeast. The amount of an EGFP protein is represented by the density and size of a band indicated with an arrow in each lane;

FIG. 23 shows the results of SDS-PAGE analysis showing the fact that the protein-producing ability of an expression vector comprising a DNA fragment having an HSP12 cold-inducible promoter function is induced in a wide low temperature range. The amount of an EGFP protein is represented by the density and size of a band indicated with an arrow in each lane;

FIG. 24 shows the results of Western blotting analysis showing the fact that a cassette comprising an HSP12 promoter, the ORF of EGFP, and a CYC1 terminator was incorporated into methylotrophic yeast, *Pichia pastoris*, so that an EGRP protein was inducibly produced in *Pichia pastoris* at a low temperature;

FIG. 25 shows the results of Western blotting analysis showing the fact that an antifreeze protein RD3 is expressed as a soluble protein by a DNA fragment having an HSP12 cold-inducible promoter function. The amount of an RD3 protein is represented by the density and size of a band in each lane; and FIG. 26 shows results obtained by expressing two types of fluorescent proteins, ECFP and DsRed by cold induction using pLTex321.

BEST MODE FOR CARRYING OUT THE INVENTION

EXAMPLES

The present invention will be further specifically described in the following examples. However, the examples are not intended to limit the technical scope of the invention.

Example 1

Identification of Cold-inducible Gene

A yeast strain, *Saccharomyces cerevisiae* YPH500 (purchased from Stratagene) was inoculated into 10 ml of YEPD medium (2% bactopeptone, 1% bactoyeast extract, 2% glucose), using an inoculating loop, followed by a shake culture at 30° C. for 2 days. 5 ml of the obtained culture solution was then inoculated into 1,000 ml of YEPD medium, followed by a shake culture at 30° C., until the absorbance at 600 nm became approximately 2 (Culture solution 1).

Fifty ml of a solution was separated from Culture solution 1, and cells were collected (a pre-low temperature treatment sample). The yeast cell mass was then frozen with liquid nitrogen, and the frozen cell mass was conserved at −80° C. in a deep freezer, until the time when RNA was prepared. The residue of Culture solution 1 was rapidly immersed in a shake water bath, which had previously been set at 10° C., and it was shaken for 30 minutes for quenching. Subsequently, the resultant product was transferred to a low temperature thermostat, which had previously been set at 10° C., and a shake culture was continuously carried out at 10° C. The time when the culture solution was immersed in a shake water bath at 10° C. was determined at 0 minute, and 50 ml each of the culture solution (a post-low temperature treatment sample) was separated by the same method as described above, 15 minutes, 30 minutes, 2 hours, 4 hours, and 8 hours later. Every time, a yeast cell mass was recovered and conserved at −80° C.

Preparation of RNA from the recovered yeast cell mass was carried out by the hot phenol method. Ten ml of an NaOAc/SDS solution (20 mM NaOAc (pH 5.5), 0.5% SDS, 1 mM EDTA), which had previously been heated to 65° C., was added to the recovered yeast cell mass. Thereafter, 20 mM NaOAc (pH 5.5)-saturated phenol, which had been heated to 65° C., was further added thereto. The mixture was fully stirred at 65° C. for 10 minutes, and it was then cooled on ice for 5 minutes. The mixture was centrifuged to recover a water phase, and 30 ml of ethanol was then added thereto, followed by cooling at −80° C. for 30 minutes. The resultant product was centrifuged to recover RNA. After a supernatant was discarded, 70% ethanol was added to the residue to wash it. The resultant product was centrifuged again, so that RNA was recovered as a precipitate. The obtained RNA was dissolved in 1 ml of NaOAc/SDS, followed by performing phenol extraction twice. Subsequently, 500 μl of 2-propanol was added thereto, and the mixture was then cooled at −80° C. for 20 minutes. Thereafter, the mixture was centrifuged to recover RNA. The residue was washed with 70% ethanol, as described above. RNA recovered as a precipitate was dissolved in 200 μl of NaOAc/SDS, and ethanol precipitation and washing with 70% ethanol were carried out, as described above. Finally, RNA was dissolved in 200 μl of distilled water. Qiagen RNeasy Mini Kit (Qiagen) was used to eliminate small molecule RNA, and RNA was purified in accordance with the protocol attached with the kit.

DNA labeled with fluorescent dye was produced using 15 μg of the thus prepared yeast total RNA and 5 μg of oligo (dT) in accordance with the manual prepared by DNA Chip Research Inc. As fluorescent dye markers, Cy3-dUTP (a pre-low temperature treatment sample) and Cy5-dUTP (a post-low temperature treatment sample), which were manufactured by Amersham Biotech, were used. Hybridization of a DNA microarray with a labeled cDNA was carried out in accordance with the manual prepared by DNA Chip Research Inc.

Hybridization was carried out. The washed DNA microarray was analyzed using GenePix4000A and Gene Pix Pro programs manufactured by Axon. The intensities of fluorescences derived from Cy3 and Cy5, which hybridized with each gene spotted on the DNA microarray, were measured. Thereafter, the obtained data was analyzed using a Gene Spring program manufactured by Silicon Genetics, so as to carry out the equalization, standardization, and time series analysis of the data. The operations were carried out in accordance with a manual attached with the program.

As a result of the analysis, a gene spot, regarding which the fluorescence intensity of Cy5 (a post-low temperature treatment sample) was 3 times or more higher than that of Cy3 (a pre-low temperature treatment sample) at any time of 15 minutes, 30 minutes, 2 hours, 4 hours, and 8 hours, was determined to be a gene controlled by a cold-inducible promoter. Using an arrangement plan of genes provided from DNA Chip Research Inc., the name of the gene was specified. The thus identified genes which are novel as a cold-inducible gene are shown in the following Table 4.

TABLE 4

Genes exhibiting 3 times or more of cold inducibility

| No. | Systematic gene name | Common name | 0.25 hr (Normalized) | 0.5 hr (Normalized) | 2 hr (Normalized) | 4 hr (Normalized) | 8 hr (Normalized) |
|---|---|---|---|---|---|---|---|
| 1 | YAL014C |  | 1.0033 | 1.38948 | 1.72818 | 2.9439597 | 4.03293 |
| 2 | YAL015C | NTG1 | 1.30889 | 1.37036 | 2.00195 | 2.6074 | 3.3652697 |
| 3 | YAL025C | MAK16 | 2.23906 | 3.4162998 | 2.42264 | 1.12295 | 0.8204 |
| 4 | YAL034C | FUN19 | 0.6976 | 0.74361 | 2.20462 | 4.08124 | 1.68092 |
| 5 | YBL048W |  | 0.88448 | 0.8266 | 1.09091 | 2.02884 | 3.3299603 |
| 6 | YBL049W |  | 1.03575 | 1.05359 | 1.34462 | 2.65459 | 4.5075 |
| 7 | YBL054W |  | 2.15287 | 3.11488 | 1.74043 | 0.62387 | 0.52929 |
| 8 | YBL056W | PTC3 | 1.1519 | 1.17583 | 2.13383 | 2.88587 | 4.9089103 |
| 9 | YBL065W |  | 0.86021 | 0.96902 | 1.54386 | 2.37517 | 4.7262497 |
| 10 | YBL078C | AUT7 | 1.18513 | 1.2101 | 1.48343 | 2.94463 | 5.8092504 |
| 11 | YBR016W |  | 0.98765 | 0.9521 | 1.62529 | 3.0799499 | 2.9415097 |
| 12 | YBR018C | GAL7 | 0.66284 | 0.62314 | 0.7807 | 1.93283 | 3.0417998 |
| 13 | YBR024W | SCO2 | 1.24344 | 1.20799 | 1.80866 | 3.0938697 | 3.6857402 |
| 14 | YBR034C | HMT1 | 2.63514 | 3.09186 | 0.81714 |  | 0.6994 |
| 15 | YBR045C | GIP1 | 0.95867 | 1.00611 | 2.66207 | 5.17561 | 3.44039 |
| 16 | YBR047W |  | 1.05117 | 0.92493 | 1.34783 | 2.19222 | 3.0629797 |
| 17 | YBR050C | REG2 | 1.54439 | 2.35019 | 4.04587 | 6.1531 | 1.82178 |
| 18 | YBR072W | HSP26 | 1.14509 | 1.03625 | 0.67711 | 1.38069 | 3.6218097 |

TABLE 4-continued

Genes exhibiting 3 times or more of cold inducibility

| No. | Systematic gene name | Common name | 0.25 hr (Normalized) | 0.5 hr (Normalized) | 2 hr (Normalized) | 4 hr (Normalized) | 8 hr (Normalized) |
|---|---|---|---|---|---|---|---|
| 19 | YBR116C | | 0.8781 | 0.90162 | 0.87838 | 5.7050705 | 7.27097 |
| 20 | YBR117C | TKL2 | 0.86577 | 0.81363 | 2 | 3.31154 | 7.0771995 |
| 21 | YBR126C | TPS1 | 0.91332 | 0.74795 | 1.15979 | 2.61072 | 3.6894302 |
| 22 | YBR148W | YSW1 | 0.89222 | 1.07221 | 1.66102 | 3.1233997 | 1.70299 |
| 23 | YBR199W | KTR4 | 1.0203 | 0.98227 | 1.44268 | 1.95379 | 3.15104 |
| 24 | YBR223C | | 0.88953 | 0.87627 | 1.36441 | 3.0317502 | 3.5880897 |
| 25 | YBR296C | PHO89 | 2.39344 | 5.2771997 | 8.24286 | 6.0016 | 1.35429 |
| 26 | YBR297W | MAL33 | 1.6135 | 2.16031 | 1.89716 | 2.53522 | 4.09979 |
| 27 | YBR298C | MAL31 | 1.03296 | 1.30158 | 1.65693 | 2.67207 | 3.10517 |
| 28 | YBR301W | | 0.87094 | 0.98242 | 1.74468 | 3.0934799 | 2.27173 |
| 29 | YCL051W | LRE1 | 0.77913 | 0.98816 | 2.06154 | 3.2779498 | 3.2061903 |
| 30 | YCR005C | CIT2 | 0.84784 | 0.8432 | 1.74417 | 2.0718 | 3.03626 |
| 31 | YCR072C | | 2.54439 | 3.15586 | 1.28448 | 0.40795 | 0.59545 |
| 32 | YCR107W | AAD3 | 1.36231 | 1.59594 | 1.75516 | 2.30492 | 4.79259 |
| 33 | YDL022W | GPD1 | 0.95536 | 0.88068 | 1.64929 | 3.97264 | 3.5084 |
| 34 | YDL024C | DIA3 | 0.88413 | 0.75221 | 1.36538 | 2.46758 | 3.6631303 |
| 35 | YDL031W | DBP10 | 1.61122 | 2.08052 | 3.27619 | 2.20487 | 1.43297 |
| 36 | YDL037C | | 3.0142403 | 2.70624 | 0.3301 | 0.14693 | 0.47497 |
| 37 | YDL039C | PRM7 | 4.11342 | 4.6858206 | 0.46122 | 0.18271 | 0.12441 |
| 38 | YDL059C | RAD59 | 1.27384 | 1.32102 | 2.01786 | 3.62362 | 6.0652 |
| 39 | YDL070W | BDF2 | 1.0365 | 1.44972 | 2.60526 | 2.71815 | 3.20639 |
| 40 | YDL075W | RPL31A | 1.56944 | 2.0143 | 3.0091102 | 2.4121 | 0.75203 |
| 41 | YDL113C | | 0.97938 | 0.92197 | 1.28113 | 2.10491 | 3.54966 |
| 42 | YDL115C | | 1.0908 | 1.15849 | 1.37566 | 1.99613 | 3.00302 |
| 43 | YDL125C | HNT1 | 1.22652 | 1.30884 | 3.05383 | 4.68391 | 8.5493 |
| 44 | YDL169C | UGX2 | 1.2128 | 1.28893 | 2.17714 | 4.49506 | 1.66542 |
| 45 | YDL204W | | 0.9393 | 0.73074 | 1.38918 | 5.69632 | 9.932331 |
| 46 | YDL243C | AAD4 | 1.45847 | 1.67523 | 1.94364 | 2.48658 | 4.03121 |
| 47 | YDR003W | | 1.04936 | 1.11417 | 1.96771 | 2.83599 | 3.64743 |
| 48 | YDR018C | | 1.08121 | 1.19178 | 1.31746 | 2.47958 | 4.25155 |
| 49 | YDR056C | | 1.15346 | 1.17336 | 2.27527 | 3.2575502 | 3.2205 |
| 50 | YDR070C | | 1.02834 | 0.86121 | 1.02092 | 4.63736 | 11.93918 |
| 51 | YDR111C | | 1.34719 | 1.391 | 1.91391 | 3.1618202 | 4.73053 |
| 52 | YDR174W | HMO1 | 1.1481 | 1.36264 | 1.92944 | 2.88877 | 3.26418 |
| 53 | YDR184C | ATC1 | 2.3198 | 3.3462002 | 1.25904 | 0.76762 | 0.6323 |
| 54 | YDR219C | | 1.14019 | 1.30057 | 2.38916 | 2.91331 | 3.7844203 |
| 55 | YDR253C | MET32 | 0.88377 | 0.92164 | 1.01786 | 1.74309 | 3.23206 |
| 56 | YDR256C | CTA1 | 1.00678 | 1.3297 | 1.0625 | 2.19923 | 5.23997 |
| 57 | YDR262W | | 1.00281 | 1.13639 | 1.90785 | 2.68828 | 3.6677098 |
| 58 | YDR306C | | 1.03452 | 0.97753 | 2.19792 | 3.3892598 | 4.26821 |
| 59 | YDR336W | | 1.46868 | 1.70028 | 2.3625 | 3.4174497 | 1.51793 |
| 60 | YDR346C | | 1.48413 | 2.06148 | 3.6093798 | 3.1203103 | 2.72309 |
| 61 | YDR387C | | 0.78635 | 0.72793 | 1.51411 | 2.63446 | 3.0599303 |
| 62 | YDR398W | | 2.50124 | 3.5828202 | 2.09428 | 0.81503 | 0.47692 |
| 63 | YDR435C | PPM1 | 1.19833 | 1.26417 | 1.83004 | 2.43209 | 3.35998 |
| 64 | YDR453C | | 1.02314 | 0.89832 | 1.0219 | 3.6123 | 4.25316 |
| 65 | YDR471W | RPL27B | 1.50493 | 2.08128 | 3.1332302 | 1.31769 | 0.42956 |
| 66 | YDR492W | | 2.58023 | 6.62935 | 13.0743 | 10.20106 | 5.89573 |
| 67 | YDR496C | | 1.93937 | 3.0013602 | 3.0263703 | 1.37132 | 0.60135 |
| 68 | YDR504C | | 1.00437 | 1.03392 | 1.58559 | 2.33226 | 3.02352 |
| 69 | YDR516C | | 0.81438 | 0.69661 | 1.57257 | 2.9018703 | 3.2232897 |
| 70 | YDR530C | APA2 | 1.02962 | 1.13114 | 1.66489 | 3.4215798 | 3.88631 |
| 71 | YDR542W | | 0.92785 | 1.2273 | 1.625 | 3.1067197 | 2.69385 |
| 72 | YEL011W | GLC3 | 0.96412 | 0.75124 | 2.88229 | 7.0288205 | 11.758249 |
| 73 | YEL039C | CYC7 | 0.92893 | 0.73858 | 1.17658 | 3.8259 | 3.18927 |
| 74 | YEL072W | | 1.19934 | 1.57944 | 4.93791 | 8.34776 | 12.152559 |
| 75 | YER020W | GPA2 | 0.95994 | 1.08487 | 2.46209 | 3.864 | 2.30808 |
| 76 | YER042W | MXR1 | 1.35873 | 1.35649 | 1.62658 | 2.16199 | 3.4200802 |
| 77 | YER053C | | 0.99461 | 0.85507 | 1.66765 | 3.3705401 | 4.5278196 |
| 78 | YER056C | FCY2 | 2.64863 | 3.2977998 | 1.35123 | 0.32066 | 0.22148 |
| 79 | YER065C | ICL1 | 1.17778 | 1.66126 | 2.44364 | 2.98419 | 4.15741 |
| 80 | YER066W | | 0.78102 | 0.87729 | 2.92213 | 4.50196 | 4.60095 |
| 81 | YER067W | | 0.50699 | 0.62875 | 3.71825 | 7.8568697 | 8.223431 |
| 82 | YER078C | | 1.03939 | 1.09121 | 2.2375 | 3.31545 | 1.94628 |
| 83 | YER079W | | 0.85437 | 0.82674 | 1.50259 | 3.6082 | 1.96935 |
| 84 | YER117W | RPL23B | 1.51201 | 1.94439 | 3.17666 | 2.00212 | 0.83311 |
| 85 | YER150W | SPI1 | 0.84877 | 0.77781 | 1.29897 | 2.80709 | 3.0019 |
| 86 | YFL014W | HSP12 | 1.20927 | 0.9725 | 0.87215 | 2.46087 | 9.3936205 |
| 87 | YFL030W | | 1.13982 | 1.11851 | 1.65561 | 2.55246 | 3.8397 |
| 88 | YFL055W | AGP3 | 1.00927 | 1.30234 | 4.47706 | 10.714099 | 18.273357 |
| 89 | YFL056C | AAD6 | 1.16193 | 1.32224 | 1.62179 | 2.41718 | 3.5401 |
| 90 | YFL057C | | 1.31235 | 1.54697 | 1.78583 | 2.65886 | 4.9862905 |
| 91 | YFR014C | CMK1 | 1.23873 | 1.40431 | 1.78136 | 2.79512 | 4.85549 |
| 92 | YFR015C | GSY1 | 0.80209 | 0.61885 | 1.56667 | 3.61418 | 2.04716 |

TABLE 4-continued

Genes exhibiting 3 times or more of cold inducibility

| No. | Systematic gene name | Common name | 0.25 hr (Normalized) | 0.5 hr (Normalized) | 2 hr (Normalized) | 4 hr (Normalized) | 8 hr (Normalized) |
|---|---|---|---|---|---|---|---|
| 93 | YFR017C | | 0.75176 | 0.65432 | 1.81091 | 3.7296097 | 4.3214703 |
| 94 | YFR053C | HXK1 | 1.0097 | 1.14979 | 3.8469803 | 4.8080006 | 4.44604 |
| 95 | YGL029W | CGR1 | 1.47899 | 2.80426 | 3.41014 | 2.20962 | 1.07818 |
| 96 | YGL033W | HOP2 | 0.88809 | 0.8757 | 0.86 | 1.82706 | 3.46097 |
| 97 | YGL045W | | 0.84499 | 0.88588 | 1.675 | 3.94022 | 3.7547197 |
| 98 | YGL075C | MPS2 | 0.92903 | 0.96407 | 1.08609 | 1.9752 | 3.1905599 |
| 99 | YGL122C | NAB2 | 0.81065 | 0.98731 | 2.9251502 | 3.3459601 | 4.15031 |
| 100 | YGL135W | RPL1B | 1.54394 | 1.91542 | 3.12628 | 2.31277 | 1.20963 |
| 101 | YGL179C | TOS3 | 0.92586 | 0.97704 | 3.6000001 | 5.87365 | 4.88168 |
| 102 | YGL184C | STR3 | 0.93984 | 0.96212 | 1.01517 | 1.91628 | 3.90721 |
| 103 | YGL255W | ZRT1 | 1.94464 | 2.8635201 | 3.5871997 | 4.1866007 | 10.74703 |
| 104 | YGL261C | | 0.93717 | 1.04224 | 1.66667 | 3.0096 | 3.47758 |
| 105 | YGR008C | STF2 | 1.01723 | 0.82271 | 2.60458 | 6.17081 | 12.13232 |
| 106 | YGR043C | | 1.10852 | 1.05999 | 1.22387 | 4.53298 | 12.765181 |
| 107 | YGR053C | | 0.87555 | 0.85445 | 1.38938 | 1.89862 | 3.0796297 |
| 108 | YGR088W | CTT1 | 0.73144 | 0.5275 | 2.61392 | 8.44166 | 9.138019 |
| 109 | YGR102C | | 1.02841 | 1.10224 | 0.92 | 1.99894 | 3.01003 |
| 110 | YGR154C | | 1.08783 | 1.16426 | 1.53119 | 2.40742 | 4.68076 |
| 111 | YGR197C | SNG1 | 1.00376 | 1.1192 | 2.2019 | 3.2474 | 3.1514597 |
| 112 | YGR222W | PET54 | 1.26054 | 1.42349 | 1.60366 | 2.08335 | 3.08212 |
| 113 | YGR223C | | 1.19349 | 1.26046 | 2.53929 | 3.2797003 | 3.1076899 |
| 114 | YGR251W | | 1.6456 | 2.2153 | 2.10687 | 1.95891 | 3.09891 |
| 115 | YGR256W | GND2 | 1.00473 | 0.91066 | 0.80725 | 1.505 | 3.26524 |
| 116 | YGR262C | | 1.1995 | 1.26261 | 1.58762 | 2.31353 | 3.66908 |
| 117 | YGR286C | BIO2 | 1.27075 | 1.81795 | 4.17834 | 4.07809 | 2.96402 |
| 118 | YGR294W | | 0.95577 | 1.15384 | 2.4 | 3.1283402 | 1.82326 |
| 119 | YHL016C | DUR3 | 0.87458 | 1.24974 | 3.37398 | 1.98922 | 1.26147 |
| 120 | YHL021C | | 0.53181 | 0.33107 | 1.4273 | 3.25184 | 3.4255702 |
| 121 | YHL036W | MUP3 | 0.96214 | 1.05319 | 2.00749 | 2.55455 | 3.1350303 |
| 122 | YHL046C | | 0.88892 | 1.08159 | 2.48555 | 3.8127797 | 3.1550698 |
| 123 | YHR066W | SSF1 | 2.03287 | 3.06945 | 1.28049 | 0.39122 | 0.42343 |
| 124 | YHR087W | | 0.96424 | 0.85725 | 1.97701 | 8.501441 | 11.07285 |
| 125 | YHR138C | | 1.38952 | 1.42322 | 3.06207 | 3.10159 | 4.42282 |
| 126 | YHR139C | SPS100 | 0.98016 | 1.02298 | 2.97178 | 10.10476 | 17.492609 |
| 127 | YHR141C | RPL42B | 1.67425 | 2.11846 | 3.2603197 | 1.71907 | 0.50346 |
| 128 | YHR146W | | 0.73244 | 1.10551 | 1.84584 | 3.1886997 | 3.3606603 |
| 129 | YIL036W | CST6 | 1.0246 | 1.11707 | 2.81361 | 3.82443 | 3.8948402 |
| 130 | YIL045W | PIG2 | 0.71006 | 0.52756 | 1.42746 | 3.0158298 | 2.69356 |
| 131 | YIL069C | RPS24B | 1.74011 | 2.2868 | 3.1866403 | 1.75181 | 0.68099 |
| 132 | YIL077C | | 1.10246 | 1.15074 | 2.4375 | 3.40083 | 2.0907 |
| 133 | YIL107C | PFK26 | 0.90527 | 0.77253 | 1.14115 | 2.4408 | 3.8814597 |
| 134 | YIL136W | OM45 | 0.84002 | 0.71072 | 0.72702 | 2.82218 | 3.83757 |
| 135 | YIL143C | SSL2 | 1.12017 | 1.16916 | 2.10938 | 2.7908301 | 3.29 |
| 136 | YIL153W | RRD1 | 0.89555 | 0.93818 | 1.50312 | 2.78051 | 3.1932 |
| 137 | YJL132W | | 0.87519 | 0.78836 | 1.25191 | 1.77312 | 3.03586 |
| 138 | YJL155C | FBP26 | 0.95693 | 0.91742 | 1.43721 | 2.23459 | 4.2299094 |
| 139 | YJL223C | PAU1 | 0.94032 | 1.07645 | 2.33929 | 4.01076 | 3.37687 |
| 140 | YJR085C | | 1.22341 | 1.13732 | 1.30019 | 1.75168 | 3.03429 |
| 141 | YJR155W | AAD10 | 1.11394 | 1.16776 | 1.52716 | 2.03351 | 3.72837 |
| 142 | YKL026C | GPX1 | 1.0308 | 0.96926 | 2.38347 | 4.73596 | 8.17473 |
| 143 | YKL070W | | 1.77472 | 3.02877 | 7.3672304 | 13.586381 | 14.590239 |
| 144 | YKL071W | | 1.36053 | 1.46881 | 1.66965 | 2.03659 | 3.51212 |
| 145 | YKL078W | | 2.37036 | 3.2950103 | 1.38636 | 0.90211 | 0.7957 |
| 146 | YKL087C | CYT2 | 1.08878 | 1.13993 | 1.52257 | 2.52182 | 4.00504 |
| 147 | YKL089W | MIF2 | 0.9988 | 0.93813 | 1.48333 | 3.3537698 | 3.56049 |
| 148 | YKL090W | | 0.95164 | 1.0171 | 1.17553 | 3.4655097 | 2.18442 |
| 149 | YKL091C | | 0.75033 | 0.54752 | 1.17633 | 3.13907 | 4.35414 |
| 150 | YKL094W | YJU3 | 1.11442 | 1.15337 | 1.49033 | 2.88253 | 5.11229 |
| 151 | YKL103C | LAP4 | 1.11797 | 1.18683 | 1.50443 | 2.29227 | 3.98024 |
| 152 | YKL125W | RRN3 | 1.28447 | 1.13671 | 1.45736 | 2.11759 | 3.15104 |
| 153 | YKL150W | MCR1 | 0.98958 | 0.91165 | 1.66348 | 3.1258898 | 4.36814 |
| 154 | YKL151C | | 1.02779 | 0.87802 | 1.28317 | 2.40705 | 3.64677 |
| 155 | YKL162C | | 0.90755 | 1.10725 | 1.61719 | 2.48505 | 5.47137 |
| 156 | YKL187C | | 0.95593 | 1.04668 | 6.15217 | 22.404268 | 15.74071 |
| 157 | YKL224C | | 0.89848 | 1.12533 | 2.81176 | 3.25963 | 2.08497 |
| 158 | YKR049C | | 1.25539 | 1.2027 | 1.75 | 3.07264 | 2.44532 |
| 159 | YKR075C | | 3.0095403 | 3.27039 | 0.50806 | 0.95682 | 0.91958 |
| 160 | YKR077W | | 1.14206 | 1.71613 | 1.91304 | 4.17779 | 2.21691 |
| 161 | YKR100C | | 0.91584 | 1.08788 | 1.70127 | 2.34189 | 3.0141 |
| 162 | YLL055W | | 1.13227 | 1.26922 | 3.6136997 | 3.98156 | 4.27876 |
| 163 | YLL056C | | 0.98863 | 1.09245 | 2.02424 | 4.75816 | 7.3932605 |
| 164 | YLR009W | | 1.60275 | 2.40353 | 3.1268404 | 1.1439 | 0.41884 |
| 165 | YLR145W | | 0.97333 | 1.2659 | 1.44364 | 4.03507 | 3.76035 |
| 166 | YLR149C | | 0.63981 | 0.81805 | 1.11078 | 2.54315 | 3.70763 |

TABLE 4-continued

Genes exhibiting 3 times or more of cold inducibility

| No. | Systematic gene name | Common name | 0.25 hr (Normalized) | 0.5 hr (Normalized) | 2 hr (Normalized) | 4 hr (Normalized) | 8 hr (Normalized) |
|---|---|---|---|---|---|---|---|
| 167 | YLR164W | | 0.7098 | 0.64934 | 1.0303 | 3.7946599 | 3.82147 |
| 168 | YLR251W | | 0.80386 | 0.68135 | 0.7995 | 1.78338 | 3.56716 |
| 169 | YLR252W | | 0.88886 | 0.75325 | 0.93727 | 1.98089 | 3.0293598 |
| 170 | YLR266C | | 1.12845 | 1.25712 | 1.67885 | 2.21115 | 3.2613397 |
| 171 | YLR311C | | 0.9542 | 1.0924 | 1.99216 | 3.5065703 | 5.76001 |
| 172 | YLR312C | | 1.12083 | 1.11103 | 2.60448 | 4.70583 | 7.24224 |
| 173 | YLR327C | | 0.69919 | 0.88948 | 1.2234 | 3.0811 | 1.38007 |
| 174 | YLR413W | | 2.57574 | 3.95178 | 3.42857 | 1.36255 | 0.67484 |
| 175 | YLR421C | RPN13 | 1.27411 | 1.25963 | 1.62864 | 2.07345 | 3.52192 |
| 176 | YML004C | GLO1 | 1.0562 | 1.13595 | 1.15769 | 2.08466 | 3.8888502 |
| 177 | YML128C | | 1.06312 | 0.88233 | 1.19443 | 3.34315 | 7.0703206 |
| 178 | YML131W | | 1.25133 | 1.36287 | 1.6693 | 2.30028 | 4.31475 |
| 179 | YMR030W | | 0.71059 | 0.81793 | 1.29167 | 3.37439 | 1.48566 |
| 180 | YMR090W | | 1.25887 | 1.12985 | 1.38467 | 2.31588 | 3.95838 |
| 181 | YMR100W | MUB1 | 0.98043 | 1.16973 | 2.1046 | 2.71536 | 3.0512598 |
| 182 | YMR105C | PGM2 | 0.93366 | 0.67889 | 0.84615 | 2.33853 | 3.23185 |
| 183 | YMR107W | | 1.05274 | 0.9975 | 3.35795 | 13.346421 | 26.729939 |
| 184 | YMR139W | RIM11 | 0.84478 | 0.8269 | 1.88423 | 2.86575 | 3.3071597 |
| 185 | YMR246W | FAA4 | 1.51515 | 2.70731 | 7.9028206 | 5.6360803 | 2.22328 |
| 186 | YMR255W | GFD1 | 0.86952 | 1.19143 | 1.6185 | 3.07659 | 1.97355 |
| 187 | YMR258C | | 0.83821 | 0.75127 | 1.81532 | 2.99214 | 3.62522 |
| 188 | YMR262W | | 0.91145 | 0.88096 | 1.56184 | 3.65197 | 3.4286199 |
| 189 | YMR271C | URA10 | 1.18771 | 1.17152 | 1.64009 | 3.0692298 | 6.2542396 |
| 190 | YMR316W | DIA1 | 1.14344 | 1.59805 | 3.15714 | 2.4773 | 3.35398 |
| 191 | YMR320W | | 1.01219 | 1.3638 | 1.81944 | 3.53727 | 1.9338 |
| 192 | YMR322C | | 1.07036 | 0.92294 | 1.04425 | 3.2590702 | 3.9411802 |
| 193 | YNL011C | | 0.78709 | 0.83233 | 1.16337 | 2.48838 | 3.23587 |
| 194 | YNL024C | | 1.46682 | 2.16135 | 4.9626203 | 6.2175603 | 3.3494 |
| 195 | YNL112W | DBP2 | 4.01042 | 6.8630104 | 6.7637796 | 3.18022 | 0.77863 |
| 196 | YNL117W | MLS1 | 1.01106 | 1.25314 | 1.05263 | 1.76615 | 3.1688 |
| 197 | YNL124W | | 1.88126 | 3.18683 | 1.20395 | 0.32775 | 0.43034 |
| 198 | YNL141W | AAH1 | 3.2322798 | 4.3802 | 2.65636 | 0.76989 | 0.63074 |
| 199 | YNL142W | MEP2 | 1.11873 | 1.76151 | 3.07634 | 1.71723 | 1.73964 |
| 200 | YNL178W | RPS3 | 1.86694 | 2.28552 | 3.26319 | 2.9932404 | 1.222 |
| 201 | YNL194C | | 0.60936 | 0.26556 | 0.54245 | 3.3947198 | 2.92208 |
| 202 | YNL195C | | 0.77047 | 0.53543 | 0.54603 | 2.8285697 | 3.674 |
| 203 | YNL213C | | 1.21604 | 1.28292 | 1.8547 | 2.64103 | 3.2764103 |
| 204 | YNL244C | SUI1 | 1.42833 | 1.67499 | 2.85473 | 3.05486 | 3.30479 |
| 205 | YNL331C | AAD14 | 1.27426 | 1.28444 | 1.46592 | 1.74846 | 3.3124697 |
| 206 | YNR039C | ZRG17 | 1.35281 | 1.43951 | 1.24797 | 1.87414 | 3.47606 |
| 207 | YNR051C | BRE5 | 1.02042 | 1.58095 | 2.44323 | 3.06008 | 3.4274 |
| 208 | YNR053C | | 2.43279 | 3.8915102 | 2.9575803 | 0.96136 | 0.70268 |
| 209 | YNR071C | | 1.4138 | 1.79554 | 2.05263 | 3.85069 | 1.97059 |
| 210 | YNR075W | COS10 | 1.01794 | 1.38808 | 3.92754 | 5.2499 | 3.21607 |
| 211 | YNR076W | PAU6 | 0.95206 | 1.06779 | 1.9951 | 3.30685 | 2.41205 |
| 212 | YOL002C | | 1.29616 | 2.15787 | 9.937701 | 10.26189 | 2.54972 |
| 213 | YOL016C | CMK2 | 0.98959 | 1.09154 | 2.51295 | 2.511 | 3.29924 |
| 214 | YOL084W | PHM7 | 0.89374 | 1.06172 | 1.34868 | 3.0450897 | 2.44176 |
| 215 | YOL101C | | 1.45019 | 2.04909 | 19.401777 | 25.94569 | 5.15477 |
| 216 | YOL108C | INO4 | 1.00123 | 1.1017 | 2.7381 | 3.71228 | 4.51399 |
| 217 | YOL116W | MSN1 | 0.85785 | 0.93227 | 1.41 | 2.236 | 3.92998 |
| 218 | YOL124C | | 2.62574 | 3.8273304 | 1.82258 | 0.59246 | 0.50758 |
| 219 | YOL127W | RPL25 | 1.43301 | 1.79808 | 3.0211596 | 2.16872 | 0.60117 |
| 220 | YOL132W | | 1.04835 | 1.24031 | 1.54286 | 3.106 | 1.38277 |
| 221 | YOL153C | | 0.5938 | 0.52128 | 1.14079 | 2.9794703 | 3.91833 |
| 222 | YOL154W | | 1.34726 | 1.6499 | 1.56098 | 3.08407 | 2.6685 |
| 223 | YOL161C | | 0.96664 | 1.03449 | 2.15876 | 3.3816001 | 2.71004 |
| 224 | YOL162W | | 0.96196 | 1.16852 | 2.69014 | 5.84978 | 2.8762603 |
| 225 | YOL163W | | 0.96778 | 1.11322 | 2.8315797 | 5.91772 | 10.61694 |
| 226 | YOL165C | AAD145 | 1.22875 | 1.30924 | 1.71266 | 2.40526 | 3.41076 |
| 227 | YOR019W | | 0.9127 | 0.89891 | 1.57069 | 3.0450897 | 2.8125703 |
| 228 | YOR031W | CRS5 | 0.99219 | 0.97751 | 1.31677 | 2.15347 | 4.49082 |
| 229 | YOR043W | WHI2 | 1.13856 | 1.49043 | 2.8123202 | 2.99276 | 3.5548503 |
| 230 | YOR095C | RKI1 | 2.54298 | 3.30516 | 2.6587 | 0.74247 | 0.51106 |
| 231 | YOR292C | | 0.8462 | 0.8146 | 1.8877 | 3.63797 | 3.36628 |
| 232 | YOR298W | | 1.13806 | 1.34351 | 2.20339 | 3.03402 | 1.37237 |
| 233 | YOR391C | | 1.02427 | 0.93243 | 1.21622 | 3.1344903 | 4.50622 |
| 234 | YOR394W | | 0.93912 | 1.01044 | 2.27089 | 3.1992402 | 3.01734 |
| 235 | YPL004C | | 0.96002 | 0.89191 | 1.30196 | 2.85464 | 4.09551 |
| 236 | YPL014W | | 0.52817 | 0.7035 | 3.98544 | 5.42407 | 2.79718 |
| 237 | YPL015C | HST2 | 0.9054 | 0.99103 | 1.71743 | 2.89551 | 3.0497203 |
| 238 | YPL043W | NOP4 | 1.46609 | 2.46296 | 3.48128 | 1.46577 | 0.92248 |
| 239 | YPL054W | LEE1 | 1.2276 | 1.48657 | 2.8826299 | 4.24342 | 4.39311 |
| 240 | YPL093W | NOG1 | 2.31796 | 3.42804 | 2.76864 | 0.35724 | 0.21256 |

TABLE 4-continued

Genes exhibiting 3 times or more of cold inducibility

| No. | Systematic gene name | Common name | 0.25 hr (Normalized) | 0.5 hr (Normalized) | 2 hr (Normalized) | 4 hr (Normalized) | 8 hr (Normalized) |
|---|---|---|---|---|---|---|---|
| 241 | YPL107W | | 1.20868 | 1.27572 | 1.78309 | 4.46614 | 4.12846 |
| 242 | YPL122C | TFB2 | 1.20815 | 1.39332 | 2.20091 | 3.24515 | 1.51419 |
| 243 | YPL149W | APG5 | 1.24369 | 1.40163 | 1.99367 | 2.35995 | 3.04209 |
| 244 | YPL171C | OYE3 | 1.23205 | 1.16524 | 1.72912 | 2.60267 | 3.9988701 |
| 245 | YPL186C | | 0.93532 | 0.73402 | 1.39045 | 4.42236 | 7.3833003 |
| 246 | YPL223C | GRE1 | 1.02493 | 0.95208 | 0.96131 | 4.45988 | 19.046879 |
| 247 | YPL224C | MMT2 | 1.10505 | 1.2202 | 1.81892 | 2.67785 | 3.53972 |
| 248 | YPL245W | | 1.25743 | 1.27819 | 1.94444 | 3.15968 | 0.71742 |
| 249 | YPL250C | ICY2 | 1.35039 | 1.62825 | 1.53159 | 1.8243 | 3.9844902 |
| 250 | YPL280W | | 1.00028 | 0.8794 | 1.08612 | 3.5273502 | 6.96237 |
| 251 | YPL281C | ERR2 | 0.85369 | 0.76881 | 0.77273 | 1.15636 | 3.3315897 |
| 252 | YPL282C | | 0.94257 | 1.01298 | 2.54118 | 3.04157 | 2.20817 |
| 253 | YPR045C | | 0.90533 | 0.81637 | 1.32194 | 2.57976 | 3.18647 |
| 254 | YPR061C | | 1.28251 | 1.48397 | 2.21667 | 2.86721 | 3.37915 |
| 255 | YPR086W | SUA7 | 1.33226 | 1.38649 | 2.12824 | 2.46114 | 3.1201 |
| 256 | YPR121W | THI22 | 0.85368 | 1.03169 | 2.96296 | 4.04236 | 2.568 |
| 257 | YPR143W | | 1.24535 | 1.88597 | 3.25366 | 2.03536 | 1.03127 |
| 258 | YPR160W | GPH1 | 0.93853 | 0.73339 | 1.57334 | 3.6765997 | 3.65112 |
| 259 | YPR200C | ARR2 | 1.19842 | 1.10383 | 1.30505 | 1.7543 | 3.19482 |

Table 4 shows: systematic gene names of yeasts; common names (only in a case where such a common name is given) (wherein, with regard to these gene names and common names, please refer to the yeast genome database (*Saccharomyces cerevisiae* genome database); and the ratios of the normalized values of fluorescence intensities of post-low temperature treatment samples at various periods of time to the normalized values of fluorescence intensities of post-low temperature treatment samples at various periods of time to the normalized values of fluorescence intensities of pre-low temperature treatment samples.

Example 2

Confirmation of Cold Inducibility of Cold-inducible Gene

In order to confirm the cold inducibility of each cold-inducible gene identified by DNA microarray analysis, Northern blotting analysis was carried out according to the method described in Sambrook et al., Molecular Cloning, Cold Spring Harbor Laboratory. In order to measure the amount of RNA by Northern blotting analysis, probe DNA used to specifically detect RNA of interest was first prepared by the polymerase chain reaction (PCR) method. In the preset example, a method of producing the DNA probe of YFL014W (HSP12), one of the cold-inducible genes identified in Example 1, will be specifically described. Using the genome DNA of a *Saccharomyces cerevisiae* YPH500 strain, and an HSP12—F primer and an HSP12—R primer complementary to nucleotide sequences in the ORF of an HSP12 gene, and applying Expand High Fidelity PCR system (Roche), an HSP12 fragment consisting of approximately 330 bases was amplified with Takara PCR Thermal Cycler NP in accordance with the manual attached therewith.

The sequences of the above primers are as follows. With regard to the positions of the primers, please refer to the above-described yeast genome database.

HSP12-F: ATGTCTGACGCAGGTAGAAAAG    (SEQ ID NO: 1)

-continued

HSP12-R: TTACTTCTTGGTTGGGTCTTCTTC    (SEQ ID NO: 2)

PCR was carried out using 100 μl of a reaction solution containing 300 nM each primer, 200 μM dNTP (a mixed solution consisting of 4 types of deoxynucleotide triphosphate), 100 ng of the genome DNA of the *Saccharomyces cerevisiae* YPH500 strain, and a buffer (1×) and 2.6 U Expand HiFi DNA polymerase attached with the Expand High Fidelity PCR system, under conditions consisting of a first step of 95° C., 2 minutes; a second step of 35 cycles consisting of 95° C., 30 seconds (denaturation), 55° C., 30 seconds (annealing), and 72° C., 1 minute (elongation); and a third step of 72° C., 5 minutes.

Subsequently, the prepared HSP12 fragment was ligated to a pT7Blue T-vector (Novagen), and *Escherichia coli* DH5α was transformed with the obtained vector. Several transformants were cultured in a test tube, and a plasmid was then prepared using Quantum Prep Plasmid MiniPrep kit (Bio-Rad). Based on a cleavage pattern made by restriction enzymes, a transformant containing a plasmid of interest was identified. Thereafter, the obtained transformant was cultured in 80 ml of a culture solution, and a plasmid was prepared using QuantumPrep Plasmid MidiPrep kit (Bio-Rad). The nucleotide sequence of the obtained HSP12 fragment was sequence using DNA sequencing kit (Applied Biosystems), and the obtained nucleotide sequence of the HSP12 fragment was compared with the nucleotide sequence of HSP12 in the genome database (*Saccharomyces cerevisiae* genome database), so as to identify it. Thereafter, an HSP12 fragment was cut out of the pT7Blue T-vector containing the HSP12 fragment, using restriction enzymes. The HSP12 fragment was then separated and recovered by agarose gel electrophoresis using low melting point agarose (FMC). The thus obtained HSP12 fragment was labeled with alkaline phosphatase, using AlkPhos Direct Labeling Module (Amersham Biotech) in accordance with the protocol attached therewith.

Likewise, with regard to YNL112W (DBP2), YGR159C (NSR1), YNL141W (AAH1), YKR075C, YGL055W (OLE1), and YFL039C (ACT1), the same above operations were carried out using primers complementary to nucleotide sequences in ORF, so as to produce a probe used in Northern blotting.

The sequences of primers are as follows.

```
Primers to DBP2
DBP2-F:
GGATGACTTACGGTGGTAGAGATC         (SEQ ID NO: 3)

DBP2-R:
AAGATACCTCTGGCGGCCAC             (SEQ ID NO: 4)

Primers to NSR1
NSR1-F:
GGTAACAAGAAGGAAGTTAAGGCTTC       (SEQ ID NO: 5)

NSR1-R:
TGTTTTCTTTGAACCAGCGAAAG          (SEQ ID NO: 6)

Primers to AAH1
AAH1-F:
GGTTTCTGTGGAGTTTTTACAGGAG        (SEQ ID NO: 7)

AAH1-R:
GCGAATATTTAGTGACTACTTCGTCC       (SEQ ID NO: 8)

Primers to YKR075C
YKR075C-F:
TGGACGATACAATAATTTCGTACCA        (SEQ ID NO: 9)

YKR075C-R:
CAACCTGGTTCCTATAAAAAATGTCTT      (SEQ ID NO: 10)

Primers to OLE1
OLE1-F:
GGAAGCTTATGCCAACTTCTGGAACTACTATT (SEQ ID NO: 11)

OLE1-R:
GGAAGCTTTTAAAAGAACTTACCAGTTTCGTAG (SEQ ID NO: 12)

Primers to ACT1
ACT1-F:
TCAAAAAGACTCCTACGTTGGTGATGAAGC   (SEQ ID NO: 13)

ACT1-R:
CATACGCGCACAAAAGCAGAGATTAGAAAC   (SEQ ID NO: 14)
```

For NSR1, AAH1, and YKR075, PCR was carried out under the same conditions as in the above amplification of the HSP12 fragment. For DBP2, PCR was carried out under the same conditions as in the above amplification of the HSP12 fragment with the exception that the annealing temperature in the second step was changed from 55° C. to 47° C. and that the elongation reaction time (72° C.) was changed from 1 minute to 1.5 minutes. For OLE1 and ACT1, PCR was carried out using 100 µl of a reaction solution containing 200 nM each primer, 200 µM dNTP, 1 µg of the genome DNA of the *Saccharomyces cerevisiae* YPH500 strain, and a 1× natural Pfu polymerase buffer (Stratagene) and 2.5 U Pfu DNA polymerase, under conditions consisting of: a first step of 94° C., 2 minutes; a second step of 25 cycles consisting of 94° C., 30 seconds (denaturation), 55° C., 30 seconds (annealing), and 72° C., 3 minutes (elongation); and a third step of 72° C., 5 minutes. It is to be noted that with regard to OLE1 and ACT1, DNA amplified by PCR was not phosphorylated, but directly subcloned into a pZErO2 vector (Invitrogen) that had previously been cleaved with EcoRV.

Figure 1:
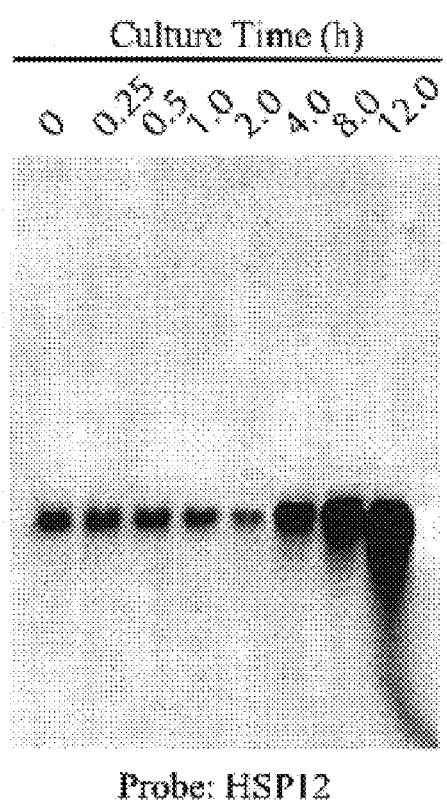
FIG. 1 shows the results of Northern blotting analysis showing a change in the amount of HSP12 mRNA obtained when the culture temperature is decreased from 30° C. to 10° C. The culture time after a low temperature treatment is shown at the top. The amount of mRNA is represented by the density and size of dots in each lane.
Figure 2:
FIG. 2 shows the results of Northern blotting analysis showing a change in the amount of DBP2 mRNA obtained when the culture temperature is decreased from 30° C. to 10° C. The culture time after a low temperature treatment is shown at the top. The amount of mRNA is represented by the density and size of dots in each lane.
Figure 3:
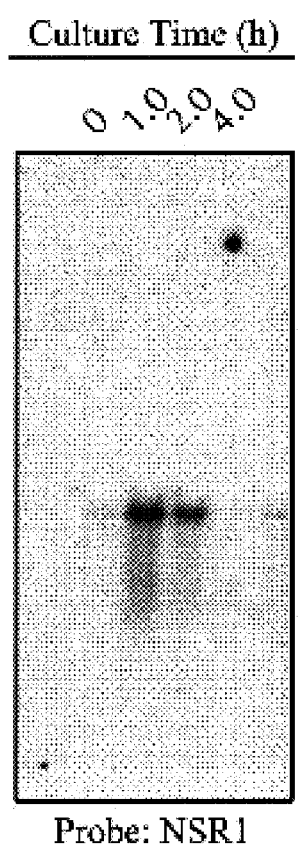
FIG. 3 shows the results of Northern blotting analysis showing a change in the amount of NSR1 mRNA obtained when the culture temperature is decreased from 30° C. to 10° C. The culture time after a low temperature treatment is shown at the top. The amount of mRNA is represented by the density and size of dots in each lane.
Figure 4:
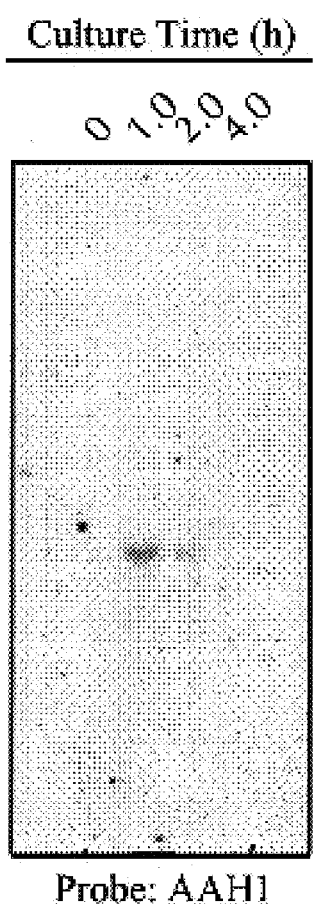
FIG. 4 shows the results of Northern blotting analysis showing a change in the amount of AAH1 mRNA obtained when the culture temperature is decreased from 30° C. to 10° C. The culture time after a low temperature treatment is shown at the top. The amount of mRNA is represented by the density and size of dots in each lane.
Figure 5:
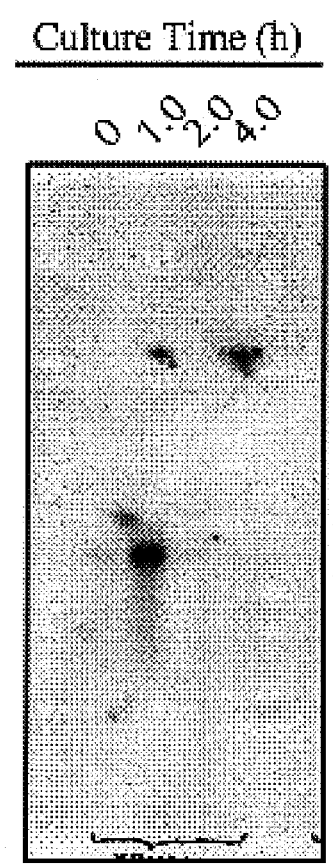
FIG. 5 shows the results of Northern blotting analysis showing a change in the amount of YKR075C mRNA obtained when the culture temperature is decreased from 30° C. to 10° C. The culture time after a low temperature treatment is shown at the top. The amount of mRNA is represented by the density and size of dots in each lane.
Figure 6:
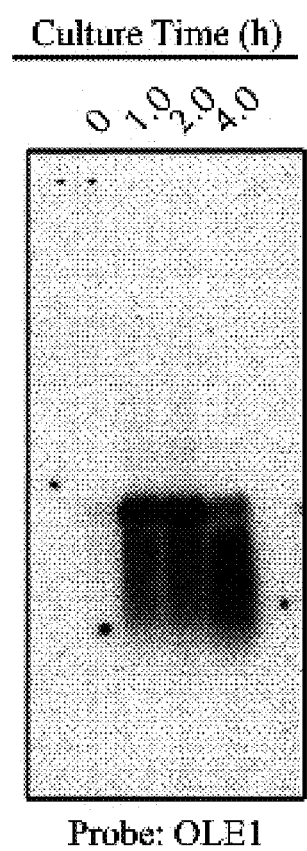
FIG. 6 shows the results of Northern blotting analysis showing a change in the amount of OLE1 mRNA obtained when the culture temperature is decreased from 30° C. to 10° C. The culture time after a low temperature treatment is shown at the top. The amount of mRNA is represented by the density and size of dots in each lane.
Figure 7:
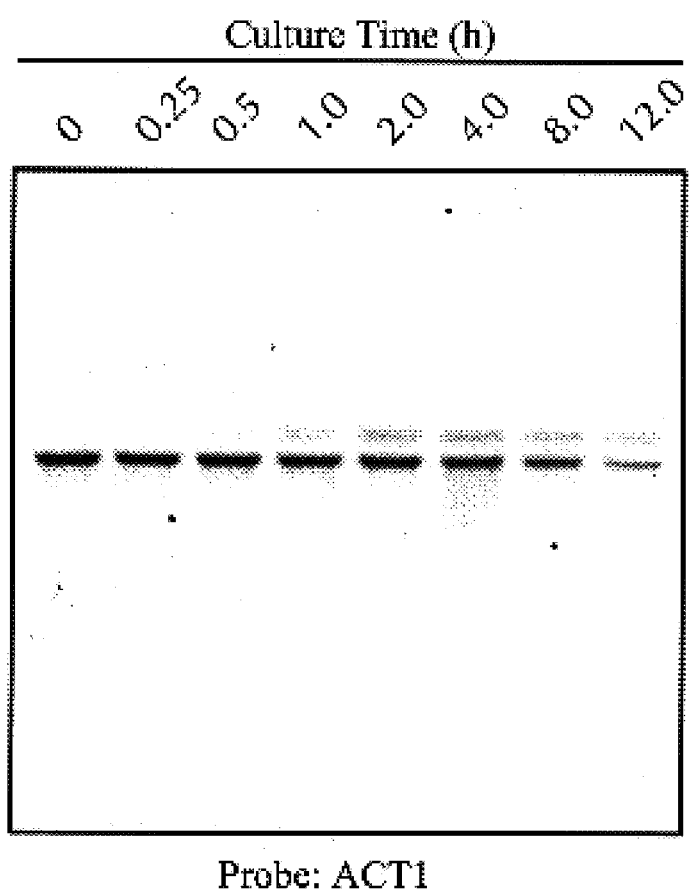
FIG. 7 shows the results of Northern blotting analysis showing a change in the amount of ACT1 mRNA obtained when the culture temperature is decreased from 30° C. to 10° C. The culture time after a low temperature treatment is shown at the top. The amount of mRNA is represented by the density and size of dots in each lane.

Subsequently, 10 µg of RNA prepared in the same manner as in Example 1 was subjected to 1% denatured agarose gel electrophoresis, and RNA was then transferred to Hybond-N+(Amersham Biotech) overnight. The obtained filter was hybridized with the labeled HSP12 fragment as prepared above in accordance with the protocol of AlkPhos Direct Labeling Module. Thereafter, using CDP-Star Detection Reagent (Amersham Biotech), the hybridized HSP12 mRNA was detected by exposure to an X-ray film, and then assayed. Likewise, using ECF Detection Module, the concentration of the purified fluorescent substance was detected with Molecular Imager FX Pro (Bio-Rad), and then assayed. The results are shown in FIG. 1. From FIG. 1, it became clear that the amount of HSP12 mRNA increased from 4 hours after the culture temperature was decreased to 10° C. Likewise, the results of Northern blotting analysis performed on DBP2, NSR1, AAH1, YKR075C, OLE1, and ACT1 are shown in FIGS. 2, 3, 4, 5, 6, and 7, respectively. In the case of DBP2, NSR1, AAH1, and YKR075C, the amount of mRNA became greater than that of a pre-low temperature treatment sample at 1 hour after the culture temperature was decreased to 10° C. In the case of OLE1 also, an increase in the amount of mRNA by a low temperature treatment was observed, and the amount of mRNA reached the maximum at 2 hours after a decrease in the culture temperature. When Northern blotting analysis was carried out on ACT1 as a negative control, the amount of mRNA of which had not been changed by a low temperature treatment in the DNA microarray, it was found that the amount of the mRNA was hardly changed by such a low temperature treatment (FIG. 7). From these results, in all the cases of HSP12, DBP2, NSR1, AAH1, YKR075C, and OLE1, an increase in the amount of mRNA by a low temperature treatment, obtained by the DNA microarray, could be confirmed by Northern blotting analysis. Accordingly, with regard to these genes, it was found that a promoter for increasing the amount of mRNA in response to a low temperature exists in the non-translation region located upstream of the 5'-terminal side of each gene.

Example 3

Cold Induction of DNA Sequence Located Downstream by DNA Fragment Having Cold-inducible Promoter Function A DNA fragment having a cold-inducible promoter function was isolated, and heterogeneous DNA was ligated downstream thereof, so that the production of RNA from DNA located downstream could be induced by a low temperature treatment. This was confirmed as follows. First, a DNA fragment having a DBP2 cold-inducible promoter function was isolated. The 5' upstream adjacent gene of DBP2 is YNL113W (RPC19). A region sandwiched between RPC19 and DBP2 (that is, a non-translation region located upstream of the 5'-terminal side of DBP2) was isolated by PCR, using two primers, each consisting of 24 bases located downstream of the 3'-terminal side adjacent to the ORF of RPC19 (RPC19-DBP2 IGR F) and 28 bases located upstream of the 5'-terminal side adjacent to the ORF of DBP2 (RPC19-DBP2 IGR R), and the genome DNA of a *Saccharomyces cerevisiae* YPH500 strain.

The sequences of the primers are as follows.

```
RPC19-DBP2 IGR F:
ATGTTACGGATCGACTCAAAGACC         (SEQ ID NO: 15)

RPC19-DBP2 IGR R:
ATTTGCTCTAAATTTGCCTTAATAGTGC     (SEQ ID NO: 16)
```

PCR was carried out under the same conditions as in the above amplification of the HSP12 fragment.

Figure 8:
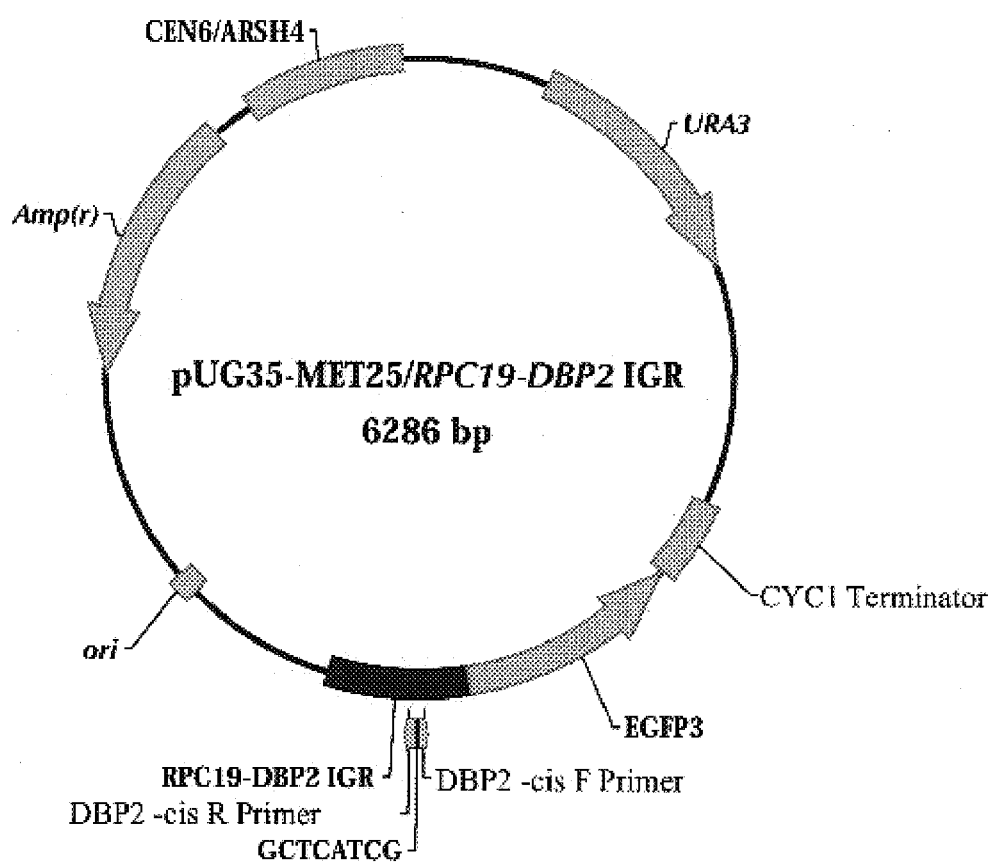
FIG. 8 shows the structure of a plasmid obtained by ligating a DNA fragment having a DBP2 promoter function upstream of the 5'-terminal side of EGFP DNA, using pUG35-MET25 as a reporter vector. The position of a DNA sequence A (GCTCATCG) and the positions of Inverse PCR primers for removing the above DNA sequence (wherein RPC19-DBP2 IGR-cis F and RPC19-DBP2 IGR-cis R are abbreviated as DBP2-cis F and DBP2-cis R, respectively) are also shown in the figure.

Subsequently, the isolated DNA was inserted into the site located upstream of the ORF of an enhanced green fluorescent protein (EGFP) in a reporter plasmid pUG35-MET25. It is to be noted that the pUG35-MET25 plasmid was produced by cleaving pUG35 with XbaI and SacI, and blunt-ending the cleaved portion with T4 DNA polymerase, followed by the self-cyclization of the obtained product. The pUG35-MET25 plasmid was cleaved with SalI, and then converted into a blunt end with T4 DNA polymerase. Thereafter, hydroxyl groups at both ends of the DNA fragment having a DBP2 cold-inducible promoter function, which had been isolated by PCR, were phosphorylated with T4 DNA kinase and ATP. The phosphorylated DNA fragment having a DBP2 promoter function was ligated to the blunt-ended pUG35-MET25 plasmid, using TaKaRa DNA Ligation Kit ver. 2 in accordance with the protocol attached with the kit. Thereafter, *Escherichia coli* DH5α was transformed with the ligated product. Several transformants as obtained above were cultured in 3 ml of a culture solution overnight, and plasmids were then prepared using QuantumPrep Plasmid MiniPrep kit. Based on a cleavage pattern made by restriction enzymes, a transformant containing a plasmid of interest was identified. In addition, at this time, a plasmid in which a DBP2 promoter is adjacent upstream of EGFP ORF (forward direction; FIG. 8), and a plasmid in which a region adjacent to an RPC19 side is ligated immediately upstream of EGFP ORF (reverse direction), were isolated. Thereafter, a transformant obtained in each case was cultured in 80 ml of a culture solution, and a plasmid was then prepared using QuantumPrep Plasmid MidiPrep kit. A yeast strain *Saccharomyces cerevisiae* YPH500 was transformed with this plasmid. Transformation was carried out by the method described in Yeast Protocol Handbook published from Invitrogen. The obtained transformed yeast was cultured at 30° C., and at the time when the absorbance at 600 nm became 1, sampling was carried out at 0 minute. Thereafter, the culture temperature was decreased from 30° C. to 10° C., and the culture was continuously carried out. Then, sampling was carried out in the same manner as described above.

Figure 9:
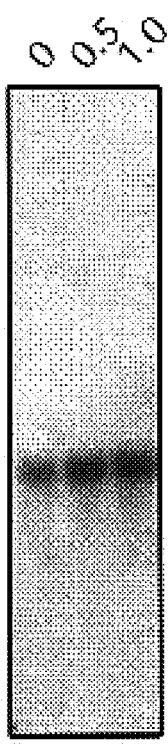
FIG. 9 shows the results of Northern blotting analysis showing a change in the amount of EGFP mRNA obtained when a DNA fragment having a DBP2 promoter function is ligated to EGFP DNA and when the culture temperature is decreased from 30° C. to 10° C. The culture time after a low temperature treatment is shown at the top. The amount of mRNA is represented by the density and size of dots in each lane.
Figure 10:
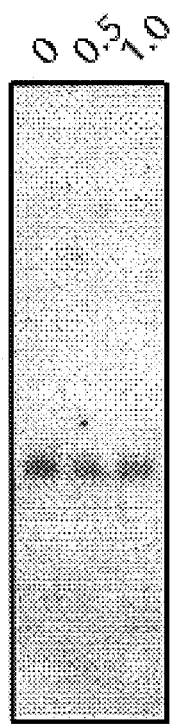
FIG. 10 shows the results of Northern blotting analysis showing a change in the amount of EGFP mRNA obtained when a DNA fragment having a DBP2 promoter function is ligated in the direction opposite to EGFP DNA and when the culture temperature is decreased from 30° C. to 10° C. The culture time after a low temperature treatment is shown at the top. The amount of mRNA is represented by the density and size of dots in each lane.

Using these samples, RNA was prepared from yeast by the same method as in Example 2, and the amount of EGFP mRNA was measured by Northern blotting analysis. A probe used in Northern blotting analysis was produced by cleaving pGFPuv (Clontech) with restriction enzymes PstI and EcoRI and recovering a GFP fragment. Northern blotting analysis was carried out by the same method as in Example 2. The results are shown in FIG. 9. From FIG. 9, it was proved that the use of a DNA fragment having a DBP2 cold-inducible promoter function promotes the transcription of DNA located downstream thereof by a low temperature treatment. Such cold inducibility was not observed, when the DNA fragment having a DBP2 cold-inducible promoter function was inserted into pUG35-MET25 in the reverse direction (FIG. 10). Thus, it was confirmed that transcriptional activation by a low temperature shown in FIG. 9 is caused by the function of a DBP2 promoter.

Likewise, with regard to DNA fragments having functions of cold-inducible promoters of YBR034C (HMT1) and YFL014W (HSP12), which were identified as cold-inducible genes in Example 1, their cold inducibility was confirmed.

First, as with the above DBP2, a DNA fragment having an HMT1 cold-inducible promoter function was isolated. The 5' upstream adjacent gene of HMT1 is YBR035C (PDX3). A region sandwiched between PDX3 and HMT1 (that is, a non-translation region located upstream of the 5'-terminal side of HMT1) was isolated by PCR, using two primers, each consisting of 25 bases located downstream of the 3'-terminal side adjacent to the ORF of PDX3 (PDX3-HMT1 IGR F) and 25 bases located upstream of the 5'-terminal side adjacent to the ORF of HMT1 (PDX3-HMT1 IGR R).

The sequences of the primers are as follows.

```
PDX3-HMT1 IGR F:
GGGACTGTTAATGAAAAATTCAATG    (SEQ ID NO: 17)

PDX3-HMT1 IGR R:
TATTTTCTTTGGATGAATTTGTCGG    (SEQ ID NO: 18)
```

PCR was carried out under the same conditions as in the above amplification of the HSP12 fragment with the exception that the annealing temperature was changed from 55° C. to 50° C. in the second step.

Figure 11:
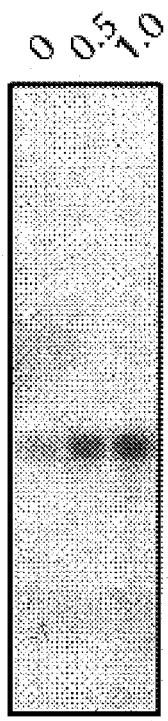
FIG. 11 shows the results of Northern blotting analysis showing a change in the amount of EGFP mRNA obtained when a DNA fragment having an HMT1 promoter function is ligated to EGFP DNA and when the culture temperature is decreased from 30° C. to 10° C. The culture time after a low temperature treatment is shown at the top. The amount of mRNA is represented by the density and size of dots in each lane.
Figure 12:
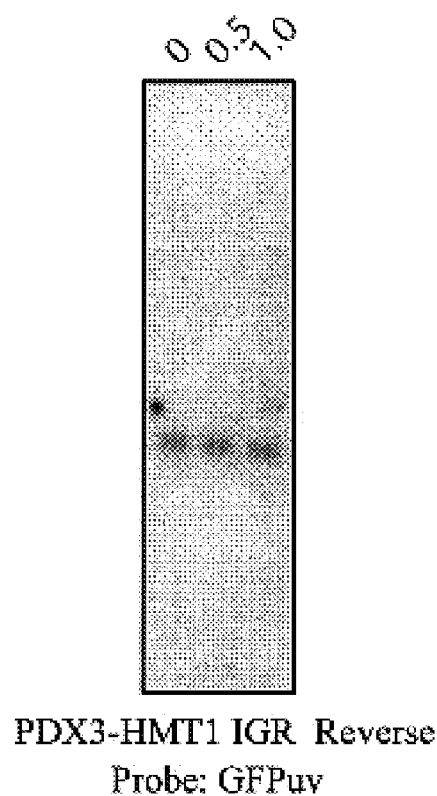
FIG. 12 shows the results of Northern blotting analysis showing a change in the amount of EGFP mRNA obtained when a DNA fragment having an HMT1 promoter function is ligated in the direction opposite to EGFP DNA and when the culture temperature is decreased from 30° C. to 10° C.

A DNA fragment having an HMT1 cold-inducible promoter function, which was obtained by the same method as in the case of the above DNA fragment having a DBP2 cold-inducible promoter function, was inserted into pUG35-MET25 (this time, a product in which the DNA fragment was inserted therein in the reverse direction was also prepared). Thereafter, cold inducibility was confirmed in the same manner as described above, using an increase in the amount of EGFP mRNA as an indicator. As a result, when the DNA fragment having an HMT1 cold-inducible promoter function was located immediately upstream of EGFP in a correct direction, cold inducibility could be confirmed (FIG. 11). However, when it was inserted therein in the reverse direction, cold inducibility was not observed (FIG. 12). From these results, it was found that the use of a DNA fragment having an HMT1 cold-inducible promoter function enables induction of the transcription of DNA located downstream thereof by a low temperature.

Thereafter, a DNA fragment having an HSP12 cold-inducible promoter function was isolated. The 5' upstream adjacent gene of HSP12 is YFL015C. However, since both genes were very close to each other and a coding region existed in the opposite chain of DNA, a region comprising a portion of the YFL015C gene and the sandwiched portion between YFL015C and HSP12 (that is, a non-translation region located upstream of the 5'-terminal side of HSP12), was isolated by PCR, using two primers, each consisting of 19 bases located in the antisense chain in the ORF of YFL015C (−610 HSP12) and 28 bases located upstream of the 5'-terminal side adjacent to the ORF of HSP12 (HSP12 IGR R).

The sequences of the primers are as follows.

```
-610 HSP12 IGR F:
GATCCCACTAACGGCCCAG          (SEQ ID NO: 19)

HSP12 IGR R:
TGTTGTATTTAGTTTTTTTGTTTTGAG  (SEQ ID NO: 20)
```

PCR was carried out under the same conditions as in the above amplification of the HSP12 fragment with the exception that the annealing temperature was changed from 55° C. to 50° C. in the second step.

A DNA fragment having an HSP12 cold-inducible promoter function, which was obtained by the same method as in the case of the above DNA fragment having a DBP2 or HMT1 cold-inducible promoter function, was inserted into pUG35-MET25 (this time, a product in which the DNA fragment was inserted therein in the reverse direction was also prepared). Thereafter, cold inducibility was confirmed in the same manner as described above, using an increase in the amount of EGFP mRNA as an indicator. As a result, when the DNA fragment having an HSP12 cold-inducible promoter function was located immediately upstream of EGFP in a correct direction, cold inducibility could be confirmed (FIG. 13). However, when it was inserted therein in the reverse direction, cold inducibility was not observed (FIG. 14). From these results, it was found that the use of a DNA fragment having an HSP12 cold-inducible promoter function enables induction of the transcription of DNA located downstream thereof by a low temperature.

Example 4

Identification of Cold-inducible Cis Sequence

A cis sequence of a DNA fragment having the cold-inducible promoter function of a gene exhibiting cold inducibility at an early stage was identified as follows. First, in the experiment described in Example 1, genes whose signal increased to 2 times or more at 15 minutes after the culture temperature was decreased to 10° C. were identified. The identified 41 genes are shown in the following Table 5.

TABLE 5

Genes exhibiting 2 times or more of cold inducibility after 15 minutes

| No. | Systematic gene name | Common name | 15 minutes (Normalized) |
| --- | --- | --- | --- |
| 1 | YDL039C | PRM7 | 4.11342 |
| 2 | YNL141W | AAH1 | 3.2322798 |
| 3 | YDL037C |  | 3.0142403 |
| 4 | YKR075C |  | 3.0095403 |
| 5 | YER056C | FCY2 | 2.64863 |
| 6 | YOL124C |  | 2.62574 |
| 7 | YDR492W |  | 2.58023 |
| 8 | YLR413W |  | 2.57574 |
| 9 | YCR072C |  | 2.54439 |
| 10 | YOR095C | RKI1 | 2.54298 |
| 11 | YNL175C | NOP13 | 2.5208 |
| 12 | YDR398W |  | 2.50124 |
| 13 | YGR283C |  | 2.40094 |
| 14 | YBR296C | PHO89 | 2.39344 |
| 15 | YDR184C | ATC1 | 2.3198 |
| 16 | YOR338W |  | 2.25481 |
| 17 | YAL025C | MAK16 | 2.23906 |
| 18 | YOR063W | RPL3 | 2.21192 |
| 19 | YIL096C |  | 2.19996 |
| 20 | YER127W | LCP5 | 2.19577 |
| 21 | YBL042C | FUI1 | 2.16603 |
| 22 | YDL063C |  | 2.16531 |
| 23 | YOR360C | PDE2 | 2.08345 |
| 24 | YHR196W |  | 2.08005 |
| 25 | YNL065W |  | 2.05877 |
| 26 | YHR066W | SSF1 | 2.03287 |
| 27 | YLR407W |  | 2.01923 |
| 28 | YOR101W | RAS1 | 2.00532 |
| 29 | YNL112W | DBP2 | 4.01042 |
| 30 | YGR159C | NSR1 | 2.9673197 |
| 31 | YGL055W | OLE1 | 2.51904 |
| 32 | YNR053C |  | 2.43279 |
| 33 | YPL093W | NOG1 | 2.31796 |
| 34 | YHR170W | NMD3 | 2.08971 |
| 35 | YHR148W | IMP3 | 2.04153 |
| 36 | YBR034C | HMT1 | 2.63514 |
| 37 | YOL010W | RCL1 | 2.46012 |
| 38 | YKL078W |  | 2.37036 |
| 39 | YMR290C | HAS1 | 2.35991 |
| 40 | YDR101C |  | 2.28186 |
| 41 | YBL054W |  | 2.15287 |

As with Table 4, Table 5 shows systematic gene names of yeasts, common names (only in a case where such a common name is given), and the ratios of the normalized values of fluorescence intensities of samples after being subjected to a low temperature treatment for 15 minutes to the normalized values of fluorescence intensities of pre-low temperature treatment samples.

Using Gene Spring (Silicon Genetics), cis sequences existing between the ORF of each of the above genes and the site 600 bp upstream thereof were searched. As a result, cis sequences could be obtained as DNA sequences that were common in some of these genes.

The cis sequences are as follows.

(a) DNA sequence A:    GCTCATCG (b) DNA sequence B:    GAGATGAG

Specifically, the above DNA sequence A was found as a cis sequence that was common in YNL112W (DBP2), YGR159C (NSR1), YGL055W (OLE1), YNR053C, YPL093W (NOG1), YHR170W (NMD3), and YHR148W (IMP3) (which correspond to Nos. 29 to 35 in Table 5), and the above DNA sequence B was found as a cis sequence that was common in YBR034C (HMT1), YOL010W (RCL1), YKL078W, YMR290C (HAS1), YDR101C, and YBL054W (which correspond to Nos. 36 to 41 in Table 5).

Example 5

Confirmation of Cold Inducibility of Cold-inducible Cis Sequences

In order to confirm that the DNA sequence A (GCTCATCG) obtained Example 4 has cold inducibility, the DNA sequence A was removed from a DNA fragment with a DBP2 cold-inducible promoter function having the above sequence, so as to confirm whether or not the cold inducibility was lost. First, the DNA fragment having a DBP2 cold-inducible promoter function prepared by PCR in Example 3 was ligated to a pT7Blue T-vector, using TaKaRa DNA Ligation Kit ver. 2. Thereafter, Escherichia coli DH5α was transformed with the obtained vector. A plasmid was prepared from the obtained transformant, and it was then sequenced, so as to confirm its nucleotide sequence. Subsequently, the plasmid as a whole, excluding the DNA sequence A, was amplified by Inverse PCR using outward primers complementary to sequences located at both ends of the DNA sequence A in the plasmid (see FIG. 8).

The sequences of the primers are as follows.

RPC19-DBP2 IGR-cis F:
CAGAAAATTTTTCCTTCAGTTTATTTG    (SEQ ID NO: 21)

RPC19-DBP2 IGR-cis R:
ATCGGCGTAAAAAAAAAAAAAAAAAAAAA    (SEQ ID NO: 22)

PCR was carried out under the same conditions as in the above amplification of the HSP12 fragment with the exception that the annealing temperature was changed from 55° C. to 50° C. and the elongation reaction time (72° C.) was changed from 1 minute to 5 minutes in the second step, and that the reaction time was changed from 5 minutes to 10 minutes in the third step.

The amplified DNA was subjected to self-circularization using TaKaRa DNA Ligation Kit ver. 2, and Escherichia coli DH5α was then transformed again with the obtained vector. Thereafter, plasmid DNA was prepared from several transformants as obtained above, and the nucleotide sequence thereof was determined. Thus, a clone was identified, from which only the DNA sequence A was removed but other nucleotide sequence portions of the DNA fragment having a DBP2 cold-inducible promoter function were not changed. Thereafter, using such a modified clone as a template, a DNA fragment having a modified DBP2 cold-inducible promoter function that was modified by the same method as in Example 3 was amplified by PCR. The amplified DNA fragment was phosphorylated, and then inserted into pUG35-MET25, so as to produce a reporter plasmid. A yeast strain, Saccharomyces cerevisiae, was transformed with this reporter plasmid, and samples were then prepared in the same manner as in Example 3, followed by performing Northern blotting analysis. The results are shown in FIG. 15. As shown in FIG. 15, when compared with the case where a native DNA fragment having a DBP2 cold-inducible promoter function was ligated upstream of EGFP DNA (FIG. 15, +cis), cold inducibility became weak by removing the DNA sequence A from the above DNA fragment (FIG. 15, −cis). Thus, it could be confirmed that it was a cis sequence in which the DNA sequence A was associated with cold induction.

Likewise, the DNA sequence B (GAGATGAG) was removed from a DNA fragment with an HMT1 cold-inducible promoter function having the above sequence, so as to confirm whether or not the cold inducibility of the DNA fragment with an HMT1 cold-inducible promoter function was lost. First, the DNA fragment having an HMT1 cold-inducible promoter function was inserted into a pT7Blue T-vector by the same method as in the case of the DNA sequence A. Then, Inverse PCR was carried out using outward primers complementary to sequences located at both ends of the DNA sequence B in the plasmid. Thereafter, the same above analysis was carried out.

The sequences of the primers are as follows.

```
PDX3-HMT1 IGR-cis F:
AACAACTATTTTTATAACATATAATTTCCC    (SEQ ID NO: 23)

PDX3-HMT1 IGR-cis R:
CTGCCTACTGCTCACCTTG               (SEQ ID NO: 24)
```

PCR was carried out under the same conditions as in the above described PCR for removing a cis sequence from the non-translation region located upstream of the 5'-terminal side of DBP2.

The results of Northern blotting analysis are shown in FIG. 16. When compared with the case where a native DNA fragment having a HMT1 cold-inducible promoter function was ligated upstream of EGFP DNA (FIG. 16, +cis), cold inducibility was lost by removing the DNA sequence B from the above DNA fragment (FIG. 16, −cis). Thus, it was confirmed that it was a cis sequence in which the DNA sequence B was associated with cold induction.

Example 6

Expression of Protein by DNA Fragment Having Cold-inducible Promoter Function, and Comparison with Other Yeast Promoters Using a DNA fragment having a cold-inducible promoter function, it was confirmed that the DNA fragment allows a foreign gene ligated downstream thereof to express. In addition, in order to demonstrate the usefulness as an expression system, a cold-inducible promoter was compared with known promoters. Specifically, a DNA fragment having an HSP12 cold-inducible promoter function was compared with an alcohol dehydrogenase (ADH1) promoter and a glyceraldehyde-3-phosphate dehydrogenase (TDH3) promoter. 3 types of expression vectors having the same plasmid structure were produced as follows, and compared.

As a plasmid comprising the DNA fragment having an HSP12 cold-inducible promoter function, the plasmid described in Example 3 was used.

A plasmid comprising an ADH1 promoter was produced as follows. First, a yeast expression vector pAAH5 having an ADH1 promoter (provided from Dr. Ryo Sato, an emeritus professor of Osaka University; Methods Enzymol. 101, 192-201 (1983)) was cleaved with SphI and HindIII. The cleaved portion was then blunt-ended with DNA Blunting Kit (Takara). Thereafter, the DNA fragment was fractionated by agarose gel electrophoresis, so as to recover a fragment containing the ADH1 promoter (approximately 400 bp). On the other hand, as in the case of the DNA fragment having an HSP12 cold-inducible promoter function, a plasmid pUG35-MET25 was cleaved with SalI, and the cleaved portion was then blunt-ended with DNA Blunting Kit, followed by performing dephosphorization with bacterial alkaline phosphatase. The above fragment containing an ADH1 promoter was ligated to the plasmid pUG35-MET25 using DNA Ligation Kit ver. 2 (Takara). Thereafter, *Escherichia coli* DH5α was transformed with the ligated product. The obtained transformant was cultured overnight. Thereafter, a plasmid was extracted using QuantumPrep Plasmid MiniPrep kit. Based on a cleavage pattern made by restriction enzymes and sequence analysis, a transformant containing a plasmid of interest was distinguished. From this transformant, an expression plasmid having an ADH1 promoter was prepared.

A plasmid comprising a TDH3 promoter was produced as follows. First, a yeast expression vector pG-3 having a TDH3 promoter (provided from Dr. Tadashi Nagashima of Shin Nihon Chemical Co., Ltd.; Methods Enzymol. 194, 389-398 (1991)) was cleaved with BamHI and HindIII. The cleaved portion was then blunt-ended with DNA Blunting Kit. Thereafter, the DNA fragment was fractionated by agarose gel electrophoresis, so as to recover a fragment containing the TDH3 promoter (approximately 660 bp). The obtained DNA fragment was inserted into the SalI site of a plasmid pUG35-MET25 by the same method as described above. A transformant having a plasmid with a structure of interest was selected, and finally, an expression plasmid having a TDH3 promoter was prepared.

These 3 types of plasmids had the same structure other than their promoters. A yeast strain *Saccharomyces cerevisiae* YPH500 was transformed with each of these 3 types of plasmids. The obtained transformed yeast was inoculated into a synthetic medium containing no uracil (0.67% yeast nitrogen base (containing no amino acid), 2% glucose, 0.02 mg/ml adenine sulfate, 0.02 mg/ml tryptophan, 0.02 mg/ml histidine, 0.03 mg/ml leucine, and 0.03 mg/ml lysine), followed by performing a shake culture at 30° C. With regard to yeast transformed with an expression plasmid comprising an ADH1 promoter and yeast transformed with an expression plasmid comprising a TDH3 promoter, a culture solution thereof was recovered at the time when the absorbance at 600 nm became approximately 1.3. With regard to yeast transformed with an expression plasmid comprising a DNA fragment having an HSP12 cold-inducible promoter function, a culture solution thereof contained in a flask was immersed in a water bath that had previously been set at 10° C., at the time when the absorbance at 600 nm became 0.5. Thereafter, while the flask was gently shaken for 15 minutes, it was quenched. The flask was then transferred into a low temperature thermostat that had previously been set at 10° C., and a shake culture was continued at 10° C. The time when the culture solution was immersed in a water bath at 10° C. was determined at 0 minute, and sampling was carried out over time. Extraction of RNA from yeast was carried out in the same manner as in Example 1. Ten μg of the prepared RNA was subjected to Northern blotting analysis by the method described in Example 2. The results are shown in FIG. 17.

The middle case in FIG. 17 shows the amount of EGFP mRNA obtained when the culture temperature for yeast transformed with 3 types of plasmids was 30° C., or when the temperature was decreased from 30° C. to 10° C. The amount of EGFP mRNA produced from the ADH1 promoter and TDH3 promoter, which are commonly used at 30° C., was compared with the amount of EGFP mRNA produced from a DNA fragment having an HSP12 cold-inducible promoter function in yeast wherein the temperature was decreased from 30° C. to 10° C. The obtained results are shown over time. The lower case in FIG. 17 shows the results obtained by comparing the amount of EGFP mRNA produced from a TDH 3 promoter, which was found to be relatively stronger than ADH1 promoter from the results of the middle case, with the amount of EGFP mRNA produced from a DNA fragment having an HSP12 cold-inducible promoter function in yeast, at 30° C., or when the temperature was decreased from 30° C. to 10° C., overtime.

From these results, it was found that a higher EGFP mRNA level was obtained when a DNA fragment having an HSP12 cold-inducible promoter function was used, than when known promoters such as an ADH1 promoter or TDH3 promoter were used.

Subsequently, the TDH3 promoter showing a higher mRNA level than that of the ADH1 promoter was used as a control, and it was compared with the DNA fragment having an HSP12 cold-inducible promoter function in terms of a protein production level. Sampling was carried out in the same manner as described above. After completion of the sampling, yeast recovered by centrifugation was added in the presence of 5 mM DTT using CelLytic™ Y (Sigma) and Protease Inhibitor Cocktail (Sigma), such that it had a concentration described in the manual attached with each of the above instruments. It was then vigorously vortexed at 4° C. for 1 hour. Subsequently, the solution was centrifuged at 4° C. at 15,000 rpm for 10 minutes. Thereafter, the supernatant was used as a total protein extract in the subsequent analysis. Thirty μg of the total protein extract was subjected to SDS-PAGE (12.5% gel) according to a common method (described in *Tanpakushitsu Jikken Note*, edited by Masato Okada and Kaori Miyazaki, Yodosha Co., Ltd., etc.). Thereafter, a protein separated by the method described in the manual was transferred to Immobilon-P (Millipore). Thereafter, using a 1,000 times diluted anti-GFP antibody (Living Colors™ A.v. Peptide Antibody, Clontech) and ECL PLUS Western Blotting Detection Kit (Amersham Biosciences), Western blotting analysis was carried out in accordance with the manual attached with each instrument, so as to detect an EGFP protein. The results are shown in FIG. 18.

The lower case in FIG. 18 shows the amount of the EGFP protein over time, which was obtained when the culture temperature for yeast transformed with a plasmid comprising a TDH3 promoter, or DNA fragment having an HSP12 cold-inducible promoter function, was decreased from 30° C. to 10° C.

From these results, it was found that a larger amount of protein could be produced when it was inducibly produced at 10° C. using a DNA fragment having an HSP12 cold-inducible promoter function, than when it was produced at 30° C. using the existing TDH3 promoter.

Example 7

Construction of Other Expression Vectors Comprising DNA Fragment Having Cold-inducible Promoter Function, and Expression of Protein by Other Types of Yeast (*Saccharomyces cerevisiae*) Strains First, various plasmids were produced by incorporating various types of restriction sites into the positions before and after EGFP. At first, using a plasmid pUG35-MET25, the ORF of EGFP was amplified by PCR.

The sequences of the used primers are as follows.

EGFP3 ORF F:
ATGTCTAAAGGTGAAGAATTATTCACTGG         (SEQ ID NO: 25)

EGFP3 ORF R:
TTATTTGTACAATTCATCCATACCATGGG         (SEQ ID NO: 26)

EGFP3 ORF F corresponded to a 29-bp downstream portion including an EGFP initiation codon ATG in the plasmid pUG35-MET25 used in Example 3. EGFP3 ORF R was a sequence complementary to a 29-bp upstream portion including an EGFP termination codon in the same above plasmid.

PCR was carried out under the same conditions as in the above amplification of the HSP12 fragment in Example 2 with the exception that 1 ng of a plasmid pUG35 was used, that the annealing temperature was set at 50° C., and that 30 cycles of reactions were carried out. The amplified DNA was phosphorylated with T4 polynucleotide kinase (Takara). On the other hand, pYES2 (purchased from Invitrogen) was cleaved with EcoRI, and the cleaved portion was then blunt-ended with DNA Blunting Kit, followed by performing dephosphorization with bacterial alkaline phosphatase. The amplified EGFP ORF was ligated to the blunt-ended pYES2 using DNA Ligation Kit ver. 2. Thereafter, *Escherichia coli* DH5α was transformed with the ligated product. The obtained transformant was cultured overnight, and a plasmid was then extracted using QuantumPrep Plasmid MiniPrep kit. Based on a cleavage pattern made by restriction enzymes, a transformant containing a plasmid of interest was identified. A plasmid pYES2+EGFP3 was prepared from this transformant.

Subsequently, in order to produce a plasmid having a centromere as a replication origin, the plasmid pYES2+EGFP3 was cleaved with HpaI and MluI, so as to recover a DNA fragment having a size of approximately 450 bp. On the other hand, pUG35-MET25 comprising the DNA fragment having an HSP12 cold-inducible promoter function produced in Example 3 (hereinafter referred to as pUG35+PHSP12) was also cleaved with HpaI and MluI. Thereafter, the above approx. 450-bp DNA fragment was ligated to the pUG35+PHSP12 (approximately 6 kb) using DNA ligation kit ver. 2. Thereafter, *Escherichia coli* DH5α was transformed with the thus ligated product. The obtained transformant was cultured overnight, and a plasmid was then extracted using QuantumPrep Plasmid MiniPrep kit. Based on a cleavage pattern made by restriction enzymes, a transformant containing a plasmid of interest was identified. A plasmid pUG35+PHSP12+MCS was prepared from this transformant.

Moreover, in order to produce a plasmid having 2μ as a replication origin, the obtained plasmid pUG35+PHSP12+MCS was cleaved with SpeI and MluI. The cleaved portion was subjected to agarose gel electrophoresis, so as to fractionate and recover an expression unit (approximately 1.6 kb). On the other hand, pYES2 was also cleaved with SpeI and MluI, and the cleaved portion was subjected to agarose gel electrophoresis, so as to fractionate and recover a pYES2 vector fragment (approximately 5.1 kb). The above expression unit was ligated to the pYES2 vector fragment using Ligation Kit ver. 2, and *Escherichia coli* DH5α was transformed with the thus ligated product. The obtained transformant was cultured overnight, and a plasmid was then extracted using QuantumPrep Plasmid MiniPrep kit. Based on a cleavage pattern made by restriction enzymes, a transformant containing a plasmid of interest was identified. A plasmid pYES2+PHSP12+EGFP3 was prepared from this transformant.

Furthermore, in order to produce a plasmid having 2μ as a replication origin and having a weak leucine synthetase gene (leu2-d), the obtained plasmid pUG35+PHSP12+MCS was cleaved with HindIII and KpnI. The cleaved portion was subjected to agarose gel electrophoresis, so as to obtain a DNA fragment (approximately 1.7 kb) containing an EGFP3 expression unit. On the other hand, pYEX-BX (purchased from AMRAD Biotech) was also cleaved with HindIII and KpnI, and the cleaved portion was subjected to agarose gel electrophoresis, so as to recover a pYEX-BX vector fragment (approximately 6.3 kb). The above DNA fragment containing the EGFP3 expression unit was ligated to the pYEX-BX vector fragment using DNA Ligation Kit ver. 2, and *Escherichia coli* DH5α was transformed with the thus ligated product. The obtained transformant was cultured overnight, and a plasmid was then extracted using QuantumPrep Plasmid MiniPrep kit. Based on a cleavage pattern made by restriction enzymes, a transformant containing a plasmid of interest was identified. A plasmid pYEX+PHSP12+EGFP3+TCYC1 was prepared from this transformant.

A yeast strain *Saccharomyces cerevisiae* YPH500 was transformed with each of these 3 types of plasmids. The obtained transformant was inoculated into a synthetic medium containing no uracil in the same manner as in Example 6, followed by performing a shake culture at 30° C. In the case of the plasmid pYEX+PHSP12+EGFP3+TCYC1, however, since it had a weak leucine synthetase gene, an experiment wherein a medium formed by removing leucine from the above synthetic medium was used was also carried out. Culture, sampling, preparation of RNA, preparation of a protein, Northern blotting analysis, and SDS-PAGE analysis were all carried out in the same manner as in Example 6.

The middle and lower cases in FIG. 19 show the amount of EGFP mRNA over time, obtained when the culture temperature for yeast transformed with these plasmids was decreased from 30° C. to 10° C. The lower case in FIG. 19 also shows the effects of removing leucine from the culture solution on the amount of the EGFP mRNA in the case of pYEX-BX.

As a result of Northern blotting analysis, in all cases of yeast transformed with 3 types of plasmids each having a different replication origin and a different selective marker (all of which comprised a DNA fragment having an HSP12 cold-inducible promoter function), the level of EGFP mRNA was increased by a low temperature treatment (10° C.).

FIG. 20 shows the amount of an EGFP protein over time, obtained when the culture temperature for yeast transformed with the plasmids shown in FIG. 19 was decreased from 30° C. to 10° C. The figure also shows the effects of removing leucine from the culture solution on the amount of the EGFP protein in the case of pYEX-BX.

As shown in FIG. 20, when the expression level of the EGFP protein in yeast transformed with each of 2 types of plasmids pUG35+PHSP12+MCS and pYEX+PHSP12+EGFP3+TCYC1 was examined by SDS-PAGE analysis, it was found that the level of the EGFP protein was increased by a low temperature treatment (10° C.) in both cases, and that a large amount of EGFP could be produced. In particular, the use of a plasmid having a leu2-d marker and a medium containing no leucine resulted in a significant production amount.

From the above studies, it was found that an expression plasmid comprising a DNA fragment having a cold-inducible promoter function enables cold-inducible production of a protein, regardless of a replication origin and a selective marker. On the other hand, it was also found that selection of such a replication origin or marker may lead to an increase in the production amount.

Subsequently, protein expression was carried out using different types of yeast strains of *Saccharomyces cerevisiae*. As such different types of yeast strains, YPH499, YPH501 (purchased from Stratagene), SHY3, KK4 (provided from Dr. Ryo Sato, an emeritus professor of Osaka University), EGY48 (purchased from Takara), and BY4741, BY4742 and BY4743 (purchased from Research Genetics) were used. These yeast strains were transformed with an expression plasmid pYEX+PHSP12+EGFP3+TCYC1. Each transformant was allowed to grow in a synthetic medium, to which necessary amino acids were added except for uracil, in the same manner as in Example 3. Thus, an intracellular protein was prepared, and analyzed by SDS-PAGE. FIG. 21 shows the amount of an EGFP protein obtained when the culture temperature was decreased from 30° C. to 10° C. for various strains transformed with pYEX+PHSP12+EGFP3+TCYC1.

Expression of EGFP was observed in all the yeast strains. Thus, it was found that the DNA fragment having an HSP12 cold-inducible promoter function acts regardless of the type of yeast strain. In particular, when EGY48 strain or BY4743 strain was used, a high production amount of EGFP was obtained.

Example 8

Comparison of Expression Vector Containing DNA Fragment Having Cold-inducible Promoter Function with Existing Expression Vectors in Terms of Expression Level pYES2 containing a galactose-inducible GAL1 promoter, pYEX-BX containing a heavy metal-inducible CUP1 promoter, and an expression plasmid pYEX+PHSP12+EGFP3+TCYC1 containing the aforementioned DNA fragment having an HSP12 cold-inducible promoter function (hereinafter referred to as pLTex221+EGFP3), were compared to one another under each recommended inducible conditions, in terms of the expression level of EGFP. The plasmid pYES2+EGFP3 produced in Example 7 was used as pYES2 containing EGFP. pYEX-BX containing EGFP was prepared as follows. The above plasmid pYES2+EGFP3 was cleaved with BamHI and XhoI, and the cleaved portion was subjected to agarose gel electrophoresis, so as to fractionate and recover EGFP3 ORF with a size of approximately 780 bp. On the other hand, pYEX-BX was cleaved with SalI and BamHI. The obtained EGFP3 ORF was ligated to pYEX-BX using DNA Ligation Kit ver. 2. Thereafter, *Escherichia coli* DH5α was transformed with the thus ligated product. The obtained transformant was cultured overnight, and a plasmid was then extracted using QuantumPrep Plasmid MiniPrep kit. Based on a cleavage pattern made by restriction enzymes, a transformant containing a plasmid of interest was identified. A plasmid pYEX-BX+EGFP3 was prepared from this transformant. A yeast strain *Saccharomyces cerevisiae* YPH500 was transformed with each of these 3 types of plasmids (pYES2+EGFP3, pYEX-BX+EGFP3, and pLTex221+EGFP3). Culture, sampling, preparation of a protein, and SDS-PAGE analysis were carried out on the obtained transformant in the same manner as in Example 6. FIG. 22 shows the results of SDS-PAGE analysis.

As shown in FIG. 22, the expression vector pLTex221+ EGFP3 containing a DNA fragment having an HSP12 cold-inducible promoter function produced a larger amount of EGFP3 than those of pYES2+EGFP3 and pYEX-BX+ EGFP3. From these results, it became clear that an expression vector containing a DNA fragment having an HSP12 cold-inducible promoter function is more excellent than the existing expression vectors.

Example 9

Cold-inducible Conditions Applied in Case of Using Expression Vector Containing DNA Fragment Having Cold-inducible Promoter Function Using a yeast strain *Saccharomyces cerevisiae* YPH500 transformed with the plasmid pYEX+PHSP12+EGFP3+ TCYC1 (pLTex221+EGFP3) produced in Example 7, cold-inducible conditions were studied. The present transformed yeast was subjected to culture, sampling, preparation of a protein, and SDS-PAGE analysis by the same methods as in Example 8. Exposure to a low temperature was carried out at 4° C., 10° C., and 20° C., and sampling was carried out at 0, 6, 12, 24, 48, 72, and 96 hours after initiation of the low temperature treatment. FIG. 23 shows the results of SDS-PAGE analysis.

As shown in FIG. 23, production of an EGFP protein was observed in all the cases of the temperatures of 4° C., 10° C., and 20° C. From these results, it was found that using a DNA fragment having an HSP12 cold-inducible promoter function, cold-inducible production of protein can be carried out by a low temperature treatment, not only at 10° C., but also at 4° C. or 20° C.

Example 10

Production of Proteins Using DNA Fragment Having Cold-inducible Promoter Function in Yeasts Other than *Saccharomyces cerevisiae*

In order to examine whether or not a DNA fragment having a cold-inducible promoter function acts in yeasts other than *Saccharomyces cerevisiae*, a DNA fragment having an HSP12 cold-inducible promoter function and EGFP3 ORF were introduced into methylotrophic yeast *Pichia pastoris*.

First, pUG35+PHSP12+MCS produced in Example 7 was cleaved with BamHI and KpnI. The cleaved portion was then subjected to agarose gel electrophoresis, so as to fractionate and recover an approx. 1.7-kb DNA fragment comprising a DNA fragment having an HSP12 cold-inducible promoter function, EGFP3 ORF, and a CYC1 terminator. On the other hand, a plasmid pPICZ-B (purchased from Invitrogen) used for *Pichia pastoris* was cleaved with BamHI and KpnI. Thereafter, the cleaved portion was subjected to agarose gel electrophoresis, so as to fractionate and recover an approx. 3.0-kb plasmid main body excluding an AOX1 terminator. The above DNA fragment was ligated to the plasmid pPICZ-B excluding the AOX1 terminator using DNA Ligation Kit ver. 2. Thereafter, *Escherichia coli* DH5α was transformed with the thus ligated product. The obtained transformant was cultured overnight, and a plasmid was then extracted using QuantumPrep Plasmid MiniPrep kit. Based on a cleavage pattern made by restriction enzymes, a transformant containing a plasmid of interest was identified. A plasmid pPICZ+PHSP12+EGFP3+TCYC1 was prepared from this transformant. A *Pichia pastoris* GS115 strain was transformed with this plasmid pPICZ+PHSP12+EGFP3+ TCYC1 in accordance with the manual attached with Easy Select *Pichia* Expression Kit (Invitrogen). Subsequently, a stain resistant to 4 mg/ml Zeocin was selected. The obtained transformant was inoculated into a YPED medium, and it was then cultured at 30° C. until the absorbance at 600 nm became 2.2. Thereafter, the culture temperature was decreased to 10° C. by the same method as in Example 6, and sampling was carried out at 3 days and 10 days after the low temperature treatment. Preparation of a protein and Western blotting analysis were carried out by the same methods as in Example 6. FIG. 24 shows the results of Western blotting analysis. FIG. 24 shows the expression of an EGFP protein observed at 3 days and 10 days after the culture temperature was decreased from 30° C. to 10° C., after the transformant *Pichia pastoris* had first been cultured at 30° C.

As shown in FIG. 24, the EGFP protein was inducibly produced by decreasing the culture temperature for methylotrophic yeast *Pichia pastoris*. From these results, it was found that the cold-inducible expression with a DNA fragment having an HSP12 cold-inducible promoter function can be carried out not only in *Saccharomyces cerevisiae* but also in other types of yeasts.

Example 11

Expression of Proteins Other than EGFP Protein Using DNA Fragment Having Cold-inducible Promoter Function The possibility of expression of proteins other than the EGFP protein using a DNA fragment having a cold-inducible promoter function was confirmed as follows. Specifically, using a DNA fragment having an HSP12 cold-inducible promoter function, cDNA of an antifreeze protein RD3 (J. Biol. Chem. 276, 1304-1310 (2001)) was ligated downstream of the aforementioned promoter. Thereafter, expression of the protein was confirmed by Western blotting analysis. It is to be noted that the RD3 protein became insolubilized, when it was allowed to express at 37° C. in an expression system using *Escherichia coli* as a host.

An expression plasmid for RD3 was produced as follows. First, a plasmid pET20b/RD3 containing RD3 ORF (provided from Dr. Yoshiyuki Nishimiya of the National Institute of Advanced Industrial Science and Technology) was cleaved with NdeI and EcoRI, and the cleaved portion was then blunt-ended with DNA Blunting Kit. The resultant product was then subjected to agarose gel electrophoresis, so as to fractionate and recover a DNA fragment containing RD3 ORF (approximately 400 bp). On the other hand, the plasmid pUG35-MET25 produced in Example 3 was cleaved with HpaI and MluI. The cleaved portion was subjected to agarose gel electrophoresis, so as to fractionate a DNA fragment and to recover a vector fragment with a size of approximately 5.4 kb. Likewise, the plasmid pYES2+EGFP3 produced in Example 7 was cleaved with HpaI and MluI. The cleaved portion was subjected to agarose gel electrophoresis, so as to fractionate and recover a fragment with a size of approximately 450 bp. The obtained vector fragment was ligated to the approx. 450-bp fragment using DNA Ligation Kit ver. 2. Thereafter, *Escherichia coli* DH5α was transformed with the thus ligated product. The obtained transformant was cultured overnight, and a plasmid was then extracted using QuantumPrep Plasmid MiniPrep kit. Based on a cleavage pattern made by restriction enzymes, a transformant containing a plasmid of interest was identified. A plasmid pUG35-MET25+MCS of interest was prepared from this transformant. This plasmid pUG35-MET25+MCS was cleaved with EcoRI and NotI. The cleaved portion was then blunt-ended with DNA Blunting Kit, followed by performing dephosphorization with bacterial alkaline phosphatase. Thereafter, the resultant product was subjected to agarose gel electrophoresis, so as to recover a vector fragment (approximately 5.1 kb). The above DNA fragment containing RD3 ORF was ligated to the above vector fragment using DNA Ligation Kit ver. 2. Thereafter, *Escherichia coli* DH5α was transformed with the ligated product. The obtained transformant was cultured overnight, and a plasmid was then extracted using QuantumPrep Plasmid MiniPrep kit. Based on a cleavage pattern made by restriction enzymes and sequence analysis, a transformant containing a plasmid of interest was identified. A plasmid pUG35-MET25+MCS+RD3 having RD3 ORF was prepared from this transformant.

Subsequently, a plasmid containing a DNA fragment having an HSP12 cold-inducible promoter function was produced. First, a DNA fragment having an HSP12 cold-inducible promoter function was amplified by PCR according to the method described in Example 4. The termini thereof were phosphorylated with T4 polynucleotide kinase, and fractionation of DNA fragments was then carried out by agarose gel electrophoresis, so as to recover a DNA fragment (approximately 610 bp) having an HSP12 cold-inducible promoter function. On the other hand, pUG35-MET25+MCS+RD3 was cleaved with SpeI. The cleaved portion was then blunt-ended with DNA Blunting Kit, followed by performing dephosphorization with bacterial alkaline phosphatase. The above DNA fragment having an HSP12 cold-inducible promoter function was ligated to the above vector fragment using DNA Ligation Kit ver. 2. Thereafter, *Escherichia coli* DH5α was transformed with the ligated product. The obtained transformant was cultured overnight, and a plasmid was then extracted using QuantumPrep Plasmid MiniPrep kit. Based on a cleavage pattern made by restriction enzymes and sequence analysis, a transformant containing a plasmid of interest was identified. Thus, an expression plasmid containing a DNA fragment having an HSP12 cold-inducible promoter function was finally prepared from this transformant.

Moreover, a plasmid containing a TDH3 promoter was produced as follows. First, a yeast expression vector pG-3 containing a TDH3 promoter was cleaved with BamHI and HindIII. The cleaved portion was then blunt-ended with DNA Blunting Kit, and fractionation of DNA fragments was carried out by agarose gel electrophoresis, so as to recover a fragment containing a TDH3 promoter (approximately 660 bp). The obtained DNA fragment was inserted into the SpeI site of pUG35-MET25+MCS+RD3 by the same method as described above. Based on a cleavage pattern made by restriction enzymes and sequence analysis, a transformant containing a plasmid having a structure of interest was selected. Thus, an expression plasmid containing a TDH3 promoter was finally prepared.

These two types of plasmids have the same structure other than their promoters. A yeast strain *Saccharomyces cerevisiae* YPH500 was transformed with each of these 2 types of plasmids. The obtained transformant was inoculated into a synthetic medium containing no uracil, followed by performing a shake culture at 30° C. With regard to yeast transformed with an expression plasmid containing a TDH3 promoter, a culture solution thereof was recovered at the time when the absorbance at 600 nm became 0.7. With regard to yeast transformed with an expression plasmid containing a DNA fragment having an HSP12 cold-inducible promoter function, culture and sampling were carried out by the same experimental methods as in Example 6 with exception that a low temperature treatment was initiated at the time when the absorbance at 600 nm became 1.0. In Western blotting analysis, a 5000 times diluted anti-RD3-N1 antibody was used (which was an antibody recognizing the subunit of RD3, which was produced by Hokudo Co., Ltd., according to our request). FIG. 25 shows the results of Western blotting analysis showing the expression level of the RD3 protein obtained when the transformed yeast was cultured, while decreasing the temperature from 30° C. to 10° C., or at 30° C. From these results, it was found that when the RD3 proteins that are insolubilized in an *Escherichia coli* expression system are inducibly produced at 10° C. using a DNA fragment having an HSP12 cold-inducible promoter function, almost the proteins are produced as soluble proteins. It could also be confirmed that the use of the DNA fragment having an HSP12 cold-inducible promoter function enables production of a larger amount of protein than the case where the protein is produced at 30° C. using the existing TDH3 promoter.

Subsequently, as in the case of RD3, ECFP and DsRed were allowed to express. In order to produce ECFP and DsRed not as fusion proteins but as natural proteins, each ORF region encoding the natural proteins from pECFP and pDsRed-Express (both of which were purchased from Clontech) was amplified by PCR, and each amplified product was then introduced into expression vectors pTrc99A (purchased from Pharmacia). *Escherichia coli* was transformed with each of these expression plasmids, but no fluorescence derived from a fluorescent protein was observed.

First, a cold-inducible expression vector pLTex321 having a multicloning site was constructed. pUG35-MET25+MCS was cleaved with ClaI and XhoI. The cleaved portion was then subjected to agarose gel electrophoresis, so as to recover a vector fragment (approximately 5.1 kbp). In order to circularize this vector fragment, the following oligo DNAs were synthesized and used as linkers.

```
MCS linker F:
                                    (SEQ ID NO: 27)
CCGCTCGAGCGGCCGCGAGCTCGTCGACATCGATGG MCS linker R:
                                    (SEQ ID NO: 28)
CCATCGATGTCGACGAGCTCGCGGCCGCTCGAGCGG
```

The linker DNAs contain a restriction site of XhoI-NotI-SacI-SalI-ClaI. Both oligo DNAs were annealed, and both termini of each of the linker DNAs were cleaved with XhoI and ClaI. The above vector fragment was ligated to the linker DNA using DNA Ligation Kit ver. 2. Thereafter, the ligated product was introduced into *Escherichia coli* DH5α. The obtained transformant was cultured overnight, and a plasmid was then extracted using QuantumPrep Plasmid MiniPrep kit. Based on a cleavage pattern made by restriction enzymes and sequence analysis, a transformant containing a plasmid of interest was identified. A plasmid of interest was prepared from this transformant.

The obtained plasmid was further cleaved with SpeI and BamHI, and the cleaved portion was subjected to agarose gel electrophoresis, so as to recover a vector fragment (approximately 5.1 kb). In order to introduce a DNA fragment having an HSP12 cold-inducible promoter function into the obtained vector fragment, a DNA fragment having an HSP12 cold-inducible promoter function and containing a SpeI recognition sequence and a BamHI recognition sequence was amplified by PCR using the primers indicated below. PCR was carried out under the same conditions as in amplification of an HSP12 fragment in Example 2.

```
-610-HSP12 IGR SpeI F:
                                      (SEQ ID NO: 29)
GGACTAGTGATCCCACTAACGGCCCAG

-610-HSP12 IGR BamHI R:
                                      (SEQ ID NO: 30)
CGGGATCCTGTTGTATTTAGTTTTTTTTGTTTTGAG
```

Thereafter, the amplified product was cleaved with SpeI and BamHI, followed by fractionation by agarose gel electrophoresis, so as to recover a DNA fragment (approximately 600 bp) having an HSP12 cold-inducible promoter function.

The above vector fragment was ligated to the DNA fragment having an HSP12 cold-inducible promoter function using DNA Ligation Kit ver. 2. Thereafter, the ligated product was introduced into *Escherichia coli* DH5α. The obtained transformant was cultured overnight, and a plasmid was then extracted using QuantumPrep Plasmid MiniPrep kit. Based on a cleavage pattern made by restriction enzymes and sequence analysis, a plasmid of interest was prepared.

The obtained plasmid was cleaved with SpeI and KpnI, and the cleaved portion was subjected to agarose gel electrophoresis, so as to recover a DNA fragment (approximately 1 kb) containing the DNA fragment having an HSP12 cold-inducible promoter function, a multicloning site, and a CYC1 terminator. Likewise, a pYEX-BX expression vector was cleaved with SpeI and KpnI, and the cleaved portion was subjected to agarose gel electrophoresis, so as to recover a vector fragment (approximately 6.4 kb). The above DNA fragment containing the DNA fragment having an HSP12 cold-inducible promoter function, a multicloning site, and a CYC1 terminator was ligated to the above vector fragment using DNA Ligation Kit ver. 2. Thereafter, the ligated product was introduced into *Escherichia coli* DH5α. The obtained transformant was cultured overnight, and a plasmid was then extracted using QuantumPrep Plasmid MiniPrep kit. Based on a cleavage pattern made by restriction enzymes and sequence analysis, an expression vector pLTex321 was prepared.

On the other hand, an expression plasmid of ECFP was produced as follows. First, ECFP ORF was prepared from a plasmid pECFP by PCR.

The sequences of the used primers were as follows.

```
BAMCFP1:
                                      (SEQ ID NO: 31)
AAAAGGATCCAAAAAAATGGTGAGCAAGGGCGAGGAG

HNDCFP2:
                                      (SEQ ID NO: 32)
TTTTAAGCTTTTACTTGTACAGCTCGTCCAT
```

BAMCFP1 comprises, in the order from the 5'-terminal side, 4 A bases, a BamHI recognition sequence, 6 A bases, and the downstream 21-bp portion from the initiation codon of ECFP ORF in pECFP. HNDCFP2 comprises, in the order from the 5'-terminal side, 4 T bases, a HindIII recognition sequence, and a sequence complementary to the upstream 21 bases from the termination codon of ECFP ORF.

PCR was carried out using 50 µl of a reaction solution containing 1 ng pECFP, 300 nM each primer, 200 µM dNTP, 1 mM $MgSO_4$, and a 1×PCR buffer used for KOD -Plus- (Toyobo Co., Ltd.) and 1U KOD -Plus- DNA polymerase, under conditions consisting of: a first step of 94° C., 2 minutes; and a second step of 30 cycles consisting of 94° C., 15 seconds (denaturation), 45° C., 30 seconds (annealing), and 68° C., 1 minute (elongation). Thereafter, the amplified DNA was cleaved with BamHI and HindIII. On the other hand, the above produced expression vector pLTex321 was cleaved with BamHI and HindIII. The ECFP ORF amplified by the above PCR was ligated to the pLTex321 vector fragment using Ligation High (Toyobo Co., Ltd.) Thereafter, the ligated product was introduced into *Escherichia coli* DH5α. The obtained transformant was cultured overnight, and a plasmid was then extracted using QuantumPrep Plasmid MiniPrep kit. Based on a cleavage pattern made by restriction enzymes and sequence analysis, a transformant containing a plasmid of interest was identified. A plasmid pLTex321+ECFP having ECFP was prepared from this transformant.

With regard to DsRed, pLTex321+DsRed was produced under the same conditions as for the above ECFP with exception that the primers indicated below were used and that pDsRed-Express was used as a template for PCR.

The sequences of the used primers are as follows.

```
BAMIRED1:
                                      (SEQ ID NO: 33)
AAAAGGATCCAAAAAAATGGCCTCCTCCGAGGACGTC

HNDRED2:
                                      (SEQ ID NO: 34)
AAAAAAGCTTCTACAGGAACAGGTGGTGGCG
```

BAMRED1 comprises, in the order from the 5'-terminal side, 4 A bases, a BamHI recognition sequence, 6 A bases, and the downstream 21-bp portion from the initiation codon of DsRed ORF in pDsRed-Express. HNDRED2 comprises, in the order from the 5'-terminal side, 4 A bases, a HindIII recognition sequence, and a sequence complementary to the upstream 21 bases from the termination codon of DsRed ORF.

A yeast strain *Saccharomyces cerevisiae* YPH500 was transformed with each of these 2 types of plasmids thus produced. The obtained transformant was inoculated into a synthetic medium containing neither uracil nor leucine, followed by performing a shake culture at 30° C. At the time when the absorbance at 600 nm became approximately 0.9, the culture product was subjected to a low temperature treatment at 10° C. Then, culture was continued at 10° C. for 24 hours. The expression of a fluorescent protein was confirmed with fluorescence under a UV lamp (356 nm). The results are shown in FIG. 26. As shown in FIG. 26, in both cases of ECFP expression yeast and DsRed expression yeast, a strong fluorescence due to the produced fluorescent protein was observed.

All publications, patents and patent applications cited herein are incorporated herein by reference in their entirety.

INDUSTRIAL APPLICABILITY

The present invention provides a DNA fragment having a cold-inducible promoter function of yeast. The DNA fragment of the present invention is useful in that it can be used in production of a protein and in regulation of production of RNA at a low temperature. The present invention enables the development of a novel protein production system utilizing advantages of a low temperature, such as production of a protein, the expression of which has previously been difficult. In addition, it is considered that the present invention promotes clarification of cold inducibility in terms of molecular mechanism.

The invention claimed is:

1. A DNA fragment that consists of a non-translation region located upstream of the 5'-terminal side of YFL014W gene of *Saccharomyces cerevisiae* and that has a cold-inducible promoter function, wherein said non-translation region is obtained by PCR-amplification using the nucleotide sequences of SEQ ID NO: 19 and SEQ ID NO: 20 as primers and *Saccharomyces cerevisiae* genomic DNA as a template.

2. An expression vector comprising the DNA fragment according to claim 1.

3. The expression vector according to claim 2, comprising a foreign gene or foreign DNA fragment downstream of said DNA fragment.

4. A transformant, which is produced by transforming a host with the expression vector according to claim 2.

5. The transformant according to claim 4, wherein said host is yeast.

6. A method for producing a protein, comprising decreasing a culture temperature and culturing the transformant according to claim 5 at the decreased temperature.

7. The method according to claim 6, wherein the culture temperature is 10° C. or lower.

8. A method for regulating RNA production, comprising decreasing a culture temperature and culturing the transformant according to claim 4 at the decreased temperature.

9. The method according to claim 8, wherein the culture temperature is 10° C. or lower.

10. A transformant, which is produced by transforming a host with the expression vector according to claim 3.

11. The transformant according to claim 10, wherein said host is yeast.

12. A method for producing a protein, comprising decreasing a culture temperature and culturing the transformant according to claim 5 at the decreased temperature.

13. The method according to claim 12, wherein the culture temperature is 10° C. or lower.

14. A method for regulating RNA production, comprising decreasing a culture temperature and culturing the transformant according to claim 5 at the decreased temperature.

15. The method according to claim 14, wherein the culture temperature is 10° C. or lower.

16. A method for producing a protein, comprising decreasing a culture temperature and culturing the transformant according to claim 10 at the decreased temperature.

17. The method according to claim 16, wherein the culture temperature is 10° C. or lower.

18. A method for regulating RNA production, comprising decreasing a culture temperature and culturing the transformant according to claim 10 at the decreased temperature.

19. The method according to claim 18, wherein the culture temperature is 10° C. or lower.

20. A method for producing a protein, comprising decreasing a culture temperature and culturing the transformant according to claim 11 at the decreased temperature.

21. The method according to claim 20, wherein the culture temperature is 10° C. or lower.

22. A method for regulating RNA production, comprising decreasing a culture temperature and culturing the transformant according to claim 11 at the decreased temperature.

23. The method according to claim 22, wherein the culture temperature is 10° C. or lower.

24. A DNA fragment that has a cold-inducible promoter function and that hybridizes under stringent conditions with a second DNA fragment comprised of a non-translation region that is located upstream of the 5'-terminal side of YFL014W gene of *Saccharomyces cerevisiae* and that has a cold-inducible promoter function, wherein said non-translation region is obtainable by PCR-amplification using the nucleotide sequences of SEQ ID NO: 19 and SEQ ID NO: 20 as primers and *Saccharomyces cerevisiae* genomic DNA as a template, and wherein said stringent conditions comprise use of (i) a hybridization solution consisting of 5×SSC comprising 0.75 M NaCl and 0.75 M sodium citrate, and 5× Denhardt's reagent comprising 0.100 ficoll 0.1% polyvinylpyrrolidone, 0.1% bovine serum albumin, and 0.1% sodium dodecyl sulfate at a temperature between 45° C. and 65° C., and (ii) washing performed in a washing solution consisting of 2×SSC and 0.1% SDS at a temperature between 45° C. and 55° C.

25. An expression vector comprising the DNA fragment according to claim 24.

26. The expression vector according to claim 25, comprising a foreign gene or foreign DNA fragment downstream of said DNA fragment.

27. A transformant, which is produced by transforming a host with the expression vector according to claim 25.

28. The transformant according to claim 27, wherein said host is yeast.

29. A method for producing a protein, comprising decreasing a culture temperature and culturing the transformant according to claim 27 at the decreased temperature.

30. The method according to claim 29, wherein the culture temperature is 10° C. or lower.

31. A method for regulating RNA production, comprising decreasing a culture temperature and culturing the transformant according to claim 27 at the decreased temperature.

32. The method according to claim 31, wherein the culture temperature is 10° C. or lower.

33. A transformant, which is produced by transforming a host with the expression vector according to claim 26.

34. The transformant according to claim 33, wherein said host is yeast.

35. A method for producing a protein, comprising decreasing a culture temperature and culturing the transformant according to claim 28 at the decreased temperature.

36. The method according to claim 35, wherein the culture temperature is 10° C. or lower.

37. A method for regulating RNA production, comprising decreasing a culture temperature and culturing the transformant according to claim 28 at the decreased temperature.

38. The method according to claim 37, wherein the culture temperature is 10° C. or lower.

39. A method for producing a protein, comprising decreasing a culture temperature and culturing the transformant according to claim 33 at the decreased temperature.

40. The method according to claim 39, wherein the culture temperature is 10° C. or lower.

41. A method for regulating RNA production, comprising decreasing a culture temperature and culturing the transformant according to claim 33 at the decreased temperature.

42. The method according to claim 41, wherein the culture temperature is 10° C. or lower.

43. A method for producing a protein, comprising decreasing a culture temperature and culturing the transformant according to claim 34 at the decreased temperature.

44. The method according to claim 43, wherein the culture temperature is 10° C. or lower.

45. A method for regulating RNA production, comprising decreasing a culture temperature and culturing the transformant according to claim 34 at the decreased temperature.

46. The method according to claim 45, wherein the culture temperature is 10° C. or lower.

* * * * *

UNITED STATES PATENT AND TRADEMARK OFFICE
CERTIFICATE OF CORRECTION

PATENT NO.          : 7,371,847 B2                                    Page 1 of 1
APPLICATION NO.  : 10/519545
DATED                  : May 13, 2008
INVENTOR(S)         : Takehiko Sahara et al.

It is certified that error appears in the above-identified patent and that said Letters Patent is hereby corrected as shown below:

IN THE CLAIMS

Please correct the following:

1. Column 59, line 55, change "claim 5" to -- claim 4 --.

2. Column 61, line 9, change "0.100 ficoll" to -- 0.1% ficoll --.

Signed and Sealed this

Fourteenth Day of October, 2008

JON W. DUDAS
*Director of the United States Patent and Trademark Office*